(12) United States Patent
Wallach et al.

(10) Patent No.: US 11,459,406 B2
(45) Date of Patent: Oct. 4, 2022

(54) NANOPARTICLES ADSORBED WITH GLIADIN MOLECULES

(71) Applicant: UNIVERSITY OF TECHNOLOGY SYDNEY, Ultimo (AU)

(72) Inventors: Michael Wallach, Ultimo (AU); Olga Shimoni, Ultimo (AU); Buket Demirci, Ultimo (AU); Anantdeep Kaur, Ultimo (AU)

(73) Assignee: UNIVERSITY OF TECHNOLOGY SYDNEY, Ultimo (AU)

( * ) Notice: Subject to any disclaimer, the term of this patent is extended or adjusted under 35 U.S.C. 154(b) by 116 days.

(21) Appl. No.: 16/485,481

(22) PCT Filed: Feb. 15, 2018

(86) PCT No.: PCT/AU2018/050125
§ 371 (c)(1),
(2) Date: Aug. 13, 2019

(87) PCT Pub. No.: WO2018/148801
PCT Pub. Date: Aug. 23, 2018

(65) Prior Publication Data
US 2020/0017604 A1 Jan. 16, 2020

(30) Foreign Application Priority Data
Feb. 15, 2017 (AU) .............................. 2017900481

(51) Int. Cl.
| G01N 33/531 | (2006.01) |
| G01N 33/543 | (2006.01) |
| C07K 17/14 | (2006.01) |
| B82Y 5/00 | (2011.01) |

(52) U.S. Cl.
CPC ........... C07K 17/14 (2013.01); G01N 33/531 (2013.01); G01N 33/54346 (2013.01); B82Y 5/00 (2013.01); G01N 2333/415 (2013.01); G01N 2800/065 (2013.01)

(58) Field of Classification Search
CPC ...... C07K 17/14; C07K 17/02; G01N 33/531; G01N 33/54346; G01N 2333/415; G01N 2800/065; G01N 2800/02; G01N 33/487; G01N 33/564; B82Y 5/00
See application file for complete search history.

(56) References Cited

PUBLICATIONS

Neves et al. "Voltametric immunosensor for the diagnosis of celiac disease based on the quantification of anti-gliadin antibodies." Sensors and Actuators B: Chemical 163(1): 253-259 (2012).
Sigma-Aldrich product specification sheet for G-3375 (wheat gliadin molecules). Retrieved from the Internet on Aug. 12, 2019: <URL: https://www.sigmaaldrich.com/Graphics/COfAInfo/SigmaSAPQM/SPEC/G3/G3375/G3375-BULK_SIGMA_.pdf>.

(Continued)

*Primary Examiner* — Tracy Vivlemore
*Assistant Examiner* — Nam P Nguyen
(74) *Attorney, Agent, or Firm* — Nixon Peabody LLP; David S. Resnick; Nicole D. Kling

(57) ABSTRACT

The present disclosure generally relates to nanoparticles adsorbed with gliadin molecules. In addition, the present disclosure relates to methods of preparing the nanoparticles adsorbed with gliadin molecules and methods of using said nanoparticles including detecting anti-gliadin 5 antibodies in a sample, diagnosing gluten-related disorders, and other applications.

11 Claims, 24 Drawing Sheets

Specification includes a Sequence Listing.

(56) References Cited

PUBLICATIONS

Molina-Delgado et al. "Usefulness of gold nanoparticles as labels for the determination of gliadins by immunochromatography with light scattering detection." Talanta 85(5): 2391-2396 (2011).
Neves et al. "Multiplexed electrochemical immunosensor for detection of celiac disease serological markers." Sensors and Actuators B 187: 33-39 (2013).

Figure 2

Solubilisation of Gliadin in Surfactants

CTAB — Cationic Surfactant

SDS — Anionic Surfactant

Comparison of size distribution of 20 nm AuNP's adsorbed with gliadin
(a) CTAB/IPA/70% Ethanol (b) SDS/IPA/70% Ethanol CTAB: Forms small micelles.
Increased solubilisation.

SDS: Forms Large micelles
Caused Aggregation 20 nm AuNP adsorbed with gliadin    A    B    C    D    E 20 nm AuNP adsorbed with gliadin    A    B    C    D    E 2 µg/mL   4 µg/mL   6 µg/mL   8 µg/mL   10 µg/mL 20 nm AuNP, A & B 20 nm AuNP with
peptide, C & D

SEQUENCE LISTING

```
<160> NUMBER OF SEQ ID NOS: 4

<210> SEQ ID NO 1
<211> LENGTH: 286
<212> TYPE: PRT
<213> ORGANISM: Triticum aestivum

<400> SEQUENCE: 1

Met Lys Thr Phe Leu Ile Leu Ala Leu Leu Ala Ile Val Ala Thr Thr
1               5                   10                  15

Ala Thr Ile Ala Val Arg Val Pro Val Pro Gln Leu Gln Pro Gln Asn
            20                  25                  30

Pro Ser Gln Gln Gln Pro Gln Lys Gln Val Pro Leu Val Gln Gln Gln
        35                  40                  45

Gln Phe Pro Gly Gln Gln Gln Pro Phe Pro Pro Gln Gln Pro Tyr Pro
    50                  55                  60

Gln Leu Gln Pro Phe Pro Ser Gln Gln Pro Tyr Met Gln Leu Gln Pro
65                  70                  75                  80
```

-continued

```
Phe Pro Gln Pro Gln Leu Pro Tyr Pro Gln Pro Gln Leu Pro Tyr Pro
                85                  90                  95

Gln Pro Gln Pro Phe Arg Pro Gln Gln Ser Tyr Pro Gln Pro Gln Pro
            100                 105                 110

Gln Tyr Ser Gln Pro Gln Gln Pro Ile Ser Gln Gln Gln Gln Gln Gln
            115                 120                 125

Gln Gln Gln Gln Ile Leu Gln Gln Ile Leu Gln Gln Gln Leu Ile Pro
        130                 135                 140

Cys Arg Asp Val Val Leu Gln Gln His Ser Ile Ala His Gly Ser Ser
145                 150                 155                 160

Gln Val Leu Gln Gln Ser Thr Tyr Gln Leu Val Gln Gln Leu Cys Cys
                165                 170                 175

Gln Gln Leu Trp Gln Ile Pro Glu Gln Ser Arg Cys Gln Ala Ile His
            180                 185                 190

Asn Val Val His Ala Ile Ile Leu His Gln Gln Gln Gln Gln Gln Gln
            195                 200                 205

Gln Gln Pro Leu Ser Gln Val Cys Phe Gln Gln Ser Arg Gln Gln Tyr
        210                 215                 220

Pro Ser Gly Gln Gly Ser Phe Gln Pro Ser Gln Gln Asn Pro Gln Ala
225                 230                 235                 240

Gln Gly Ser Val Gln Pro Gln Leu Pro Gln Phe Glu Glu Ile Arg
                245                 250                 255

Asn Leu Ala Leu Glu Thr Leu Pro Ala Met Cys Asn Val Tyr Ile Pro
                260                 265                 270

Pro Tyr Cys Thr Ile Ala Pro Val Gly Ile Phe Gly Thr Asn
            275                 280                 285
```

<210> SEQ ID NO 2
<211> LENGTH: 607
<212> TYPE: PRT
<213> ORGANISM: Bos taurus
<220> FEATURE:
<221> NAME/KEY: misc_feature
<223> OTHER INFORMATION: Bovine serum albumin

<400> SEQUENCE: 2

```
Met Lys Trp Val Thr Phe Ile Ser Leu Leu Leu Leu Phe Ser Ser Ala
1               5                   10                  15

Tyr Ser Arg Gly Val Phe Arg Arg Asp Thr His Lys Ser Glu Ile Ala
            20                  25                  30

His Arg Phe Lys Asp Leu Gly Glu Glu His Phe Lys Gly Leu Val Leu
        35                  40                  45

Ile Ala Phe Ser Gln Tyr Leu Gln Gln Cys Pro Phe Asp Glu His Val
    50                  55                  60

Lys Leu Val Asn Glu Leu Thr Glu Phe Ala Lys Thr Cys Val Ala Asp
65                  70                  75                  80

Glu Ser His Ala Gly Cys Glu Lys Ser Leu His Thr Leu Phe Gly Asp
                85                  90                  95

Glu Leu Cys Lys Val Ala Ser Leu Arg Glu Thr Tyr Gly Asp Met Ala
            100                 105                 110

Asp Cys Cys Glu Lys Gln Glu Pro Glu Arg Asn Glu Cys Phe Leu Ser
        115                 120                 125

His Lys Asp Asp Ser Pro Asp Leu Pro Lys Leu Lys Pro Asp Pro Asn
    130                 135                 140

Thr Leu Cys Asp Glu Phe Lys Ala Asp Glu Lys Lys Phe Trp Gly Lys
145                 150                 155                 160
```

```
Tyr Leu Tyr Glu Ile Ala Arg Arg His Pro Tyr Phe Tyr Ala Pro Glu
            165                 170                 175

Leu Leu Tyr Tyr Ala Asn Lys Tyr Asn Gly Val Phe Gln Glu Cys Cys
            180                 185                 190

Gln Ala Glu Asp Lys Gly Ala Cys Leu Leu Pro Lys Ile Glu Thr Met
            195                 200                 205

Arg Glu Lys Val Leu Ala Ser Ser Ala Arg Gln Arg Leu Arg Cys Ala
            210                 215                 220

Ser Ile Gln Lys Phe Gly Glu Arg Ala Leu Lys Ala Trp Ser Val Ala
225                 230                 235                 240

Arg Leu Ser Gln Lys Phe Pro Lys Ala Glu Phe Val Glu Val Thr Lys
            245                 250                 255

Leu Val Thr Asp Leu Thr Lys Val His Lys Glu Cys Cys His Gly Asp
            260                 265                 270

Leu Leu Glu Cys Ala Asp Asp Arg Ala Asp Leu Ala Lys Tyr Ile Cys
            275                 280                 285

Asp Asn Gln Asp Thr Ile Ser Ser Lys Leu Lys Glu Cys Cys Asp Lys
            290                 295                 300

Pro Leu Leu Glu Lys Ser His Cys Ile Ala Glu Val Glu Lys Asp Ala
305                 310                 315                 320

Ile Pro Glu Asn Leu Pro Pro Leu Thr Ala Asp Phe Ala Glu Asp Lys
            325                 330                 335

Asp Val Cys Lys Asn Tyr Gln Glu Ala Lys Asp Ala Phe Leu Gly Ser
            340                 345                 350

Phe Leu Tyr Glu Tyr Ser Arg Arg His Pro Glu Tyr Ala Val Ser Val
            355                 360                 365

Leu Leu Arg Leu Ala Lys Glu Tyr Glu Ala Thr Leu Glu Glu Cys Cys
            370                 375                 380

Ala Lys Asp Asp Pro His Ala Cys Tyr Ser Thr Val Phe Asp Lys Leu
385                 390                 395                 400

Lys His Leu Val Asp Glu Pro Gln Asn Leu Ile Lys Gln Asn Cys Asp
            405                 410                 415

Gln Phe Glu Lys Leu Gly Glu Tyr Gly Phe Gln Asn Ala Leu Ile Val
            420                 425                 430

Arg Tyr Thr Arg Lys Val Pro Gln Val Ser Thr Pro Thr Leu Val Glu
            435                 440                 445

Val Ser Arg Ser Leu Gly Lys Val Gly Thr Arg Cys Cys Thr Lys Pro
450                 455                 460

Glu Ser Glu Arg Met Pro Cys Thr Glu Asp Tyr Leu Ser Leu Ile Leu
465                 470                 475                 480

Asn Arg Leu Cys Val Leu His Glu Lys Thr Pro Val Ser Glu Lys Val
            485                 490                 495

Thr Lys Cys Cys Thr Glu Ser Leu Val Asn Arg Arg Pro Cys Phe Ser
            500                 505                 510

Ala Leu Thr Pro Asp Glu Thr Tyr Val Pro Lys Ala Phe Asp Glu Lys
            515                 520                 525

Leu Phe Thr Phe His Ala Asp Ile Cys Thr Leu Pro Asp Thr Glu Lys
            530                 535                 540

Gln Ile Lys Lys Gln Thr Ala Leu Val Glu Leu Leu Lys His Lys Pro
545                 550                 555                 560

Lys Ala Thr Glu Glu Gln Leu Lys Thr Val Met Glu Asn Phe Val Ala
            565                 570                 575
```

```
                                    -continued

Phe Val Asp Lys Cys Cys Ala Ala Asp Asp Lys Glu Ala Cys Phe Ala
            580                 585                 590

Val Glu Gly Pro Lys Leu Val Val Ser Thr Gln Thr Ala Leu Ala
        595                 600                 605

<210> SEQ ID NO 3
<211> LENGTH: 17
<212> TYPE: PRT
<213> ORGANISM: Artificial sequence
<220> FEATURE:
<223> OTHER INFORMATION: Gliadin peptide

<400> SEQUENCE: 3

Gln Leu Gln Pro Phe Pro Gln Pro Gln Leu Pro Tyr Pro Gln Pro Gln
1               5                   10                  15

Cys

<210> SEQ ID NO 4
<211> LENGTH: 16
<212> TYPE: PRT
<213> ORGANISM: Triticum aestivum

<400> SEQUENCE: 4

Gln Leu Gln Pro Phe Pro Gln Pro Gln Leu Pro Tyr Pro Gln Pro Gln
1               5                   10                  15
```

NANOPARTICLES ADSORBED WITH GLIADIN MOLECULES

CROSS-REFERENCE TO RELATED APPLICATIONS

This application is a 35 U.S.C. § 371 National Phase Entry Application of International Application No. PCT/AU2018/050125 filed Feb. 15 2018, which designates the U.S. and claims benefit under 35 U.S.C. § 119(a) of AU Provisional Application 2017900481 filed Feb. 15, 2017, the contents of which are incorporated herein by reference in their entireties.

SEQUENCE LISTING

The instant application contains a Sequence Listing which has been submitted electronically in ASCII format and is hereby incorporated by reference in its entirety. Said ASCII copy, created on Aug. 12, 2019, is named Sequence_Listing-053826-095800USPX.txt and is 8,516 bytes in size.

TECHNICAL FIELD

The present disclosure generally relates to nanoparticles adsorbed with gliadin molecules. In addition, the present disclosure relates to methods of preparing the nanoparticles adsorbed with gliadin molecules and methods of using said nanoparticles including detecting anti-gliadin antibodies in a sample, diagnosing gluten-related disorders, and other applications.

BACKGROUND

Gluten is a general term for polypeptides found in cereals such as wheat, barley and rye. In wheat, protein fractions of gluten include gliadins and glutenins. Gliadins are monomeric proteins that are grouped into four types: alpha, beta, gamma, or omega gliadins. Glutenins are larger polymers maintained by interchain disulphide bridges and are classified into high-molecular-weight and low-molecular-weight glutenins.

For individuals with gluten-related disorders such as coeliac disease and gluten sensitivity, consumption of gluten-containing foods can have severe and long-lasting health consequences.

Coeliac disease is a chronic disorder of the upper small intestine triggered by the ingestion of gluten. The prevalence of coeliac disease in western populations appears to be approximately 1:80 to 1:100 (Lock et al. Clin Exp Immunol 116: 258-262, 1999). This makes coeliac disease one of the most common food-related disorders worldwide. Coeliac disease patients show varying degrees of chronic inflammation within the small intestine characterised by distinct histological features such as severe villous atrophy, intra-epithelial lymphocyte infiltration and crypt hyperplasia (Oberhuber et al. Eur J Gastroenterol Hepatol 11: 1185-1194, 1999).

The detection and diagnosis of gluten-related disorders such as coeliac disease has traditionally relied on invasive methods using biopsies and histological examination of the small intestine. Such methods are inconvenient as they rely on the isolation of a tissue sample from the patient, which may require the patient to be admitted to a hospital or healthcare clinic. The procedure requires the presence of a healthcare professional, and can prove to be painful, time-consuming and expensive. Additionally, laboratory tests such as serological tests specific for coeliac specific antibodies have been used to detect anti-gliadin antibodies and to aid in the diagnosis of gluten-related disorders such as coeliac disease. However, serological tests can be relatively expensive to perform, and often involve the application of multiple analytical methods such as ELISA and indirect immunofluorescence, which are often not consistent, accurate and/or reliable. The use of multiple analytical methods can also result in a longer time for a patient to obtain results of the test. A more rapid, cost effective, accurate and improved method of detecting anti-gliadin antibodies would be beneficial.

SUMMARY

The present inventors have shown that nanoparticles adsorbed with gliadin molecules are useful for detecting antibodies in a sample, e.g., a sample from an individual suffering from a gluten-related disorder. For example, the inventors have found that changes to one or more physical properties of the nanoparticles, e.g., optical properties, occur in the presence of antibodies produced by individuals suffering from gluten-related disorders. These findings provide the basis for a rapid, inexpensive method for detecting anti-gliadin antibodies in a sample. The present inventors have further produced a simple, non-invasive means for diagnosing gluten-related disorders generally, as well as specific types of gluten related disorders, e.g., coeliac disease, dermatitis herpetiformis and gluten ataxia.

Accordingly, the present disclosure provides a nanoparticle adsorbed with a gliadin molecule. Preferably, the gliadin molecule retains sufficient conformational similarity to naturally occurring gliadin to be bound by an immuno-globulin that is capable of binding specifically to naturally occurring gliadin.

The nanoparticle as disclosed herein may be any nanoparticle known in the art to be suitable for adsorption to a gliadin molecule. In one example, the nanoparticle is a gold nanoparticle (AuNP).

The nanoparticle may have a diameter of about 1 nm to about 300 nm. In one example, the nanoparticle has a diameter of about 1 nm to about 20 nm. In another example, the nanoparticle has a diameter of about 5 nm to about 20 nm. In another example, the nanoparticle has a diameter of about 20 nm to about 80 nm. In yet another example, the nanoparticle has a diameter of about 20 nm.

The gliadin molecule may be obtained from wheat or related grains. Preferably, the gliadin molecule is a gliadin extract from wheat. In one example, the gliadin molecule is derived from the common wheat *Triticum aestivum*. An example of a suitable gliadin molecule is provided in SEQ ID NO: 1.

In another example, the gliadin molecule may comprise or consist of a gliadin protein, peptide, epitope or a fragment thereof. The peptide may be of any particular length, for example at least 5, at least 6, at least 7, at least 8, at least 9, at least 10, at least 11, at least 12, at least 13, at least 14, at least 15, at least 16, at least 17, at least 18, at least 19 or at least 20 amino acids. The peptide may be no more than, for example, 40, 30, 25, 20, 19, 18, 17, 16, 15, 14, 13, 12, 11, 10, 9, 8, 7, 6, or 5 amino acids. The peptide may be from 5 to 15, or 5 to 20, or 10 to 20, or 10 to 15, or 15 to 20 amino acids in length. An example of a gliadin peptide is a peptide comprising or consisting of the sequence QLQPFPQPQLPYPQPQC (SEQ ID NO: 3). Another example of a gliadin peptide is a peptide comprising or consisting of the sequence QLQPFPQPQLPYPQPQ (SEQ ID NO: 4). In another example, the gliadin peptide may be at least 70%, at least 80%, at least 90%, at least 95%, at least 98%, at least 99%, or 100% identical to QLQPFPQPQLPYPQPQC (SEQ ID NO: 3) or QLQPFPQPQLPYPQPQ (SEQ ID NO: 4).

The inventors have also developed an improved method for the adsorption of gliadin molecules onto nanoparticles. Thus, the present disclosure provides a method of preparing a nanoparticle as disclosed herein, the method comprising: (a) dissolving a gliadin molecule in a solution comprising a cationic surfactant and a polar protic solvent, (b) adding a nanoparticle to the solution obtained in step (a) to form a mixture; and (c) isolating a nanoparticle adsorbed with a gliadin molecule from the mixture obtained in step (b).

In one example, the cationic surfactant is cetyl trimethylammonium bromide. The polar protic solvent may be isopropanol. In one example, the cationic surfactant is cetyl trimethylammonium bromide and the polar protic solvent is isopropanol.

In another example, the method comprises heating the solution obtained in step (a) to a temperature from about 40° C. to about 80° C. In another example, the method comprises filtering the solution prior to step (b). In another example, the method comprises re-dispersing the nanoparticle in a solution prior to step (c). The solution may comprise or consist of purified water. In another example, the method comprises incubating the mixture obtained in step (b) for at least 30 minutes prior to step (c), such as for about 60 minutes prior to step (c). In one example, step (c) comprises centrifugation. Any of these method steps can be used together, in any combination.

In another example, the present disclosure provides a nanoparticle adsorbed with a gliadin molecule produced according to a method as disclosed herein.

In another example, the present disclosure provides a method of detecting an anti-gliadin antibody in a sample, the method comprising (i) contacting the sample of a body fluid obtained from an individual with a nanoparticle adsorbed with a gliadin molecule as disclosed herein, and (ii) detecting an optical property of the nanoparticle adsorbed with a gliadin molecule, wherein a change in the optical property of the nanoparticle adsorbed with a gliadin molecule is indicative of the presence of an anti-gliadin antibody in the sample.

The body fluid may be, for example, saliva, serum, blood, urine or a gastrointestinal secretion. Preferably, the body fluid is saliva. In another preferred embodiment, the body fluid is serum.

In one example, the optical property of the nanoparticle adsorbed with a gliadin molecule is absorbance. Any method known in the art for detecting changes in absorbance may be used. In one example, the change in the optical property of the nanoparticle adsorbed with a gliadin molecule as disclosed herein is detected in the ultraviolet-visible absorption spectrum. In another example, the change in the optical property of the nanoparticle adsorbed with a gliadin molecule as disclosed herein is detected in the visible absorption spectrum.

In another example, the change in the optical property of the nanoparticle adsorbed with a gliadin molecule as disclosed herein is detected within less than about thirty minutes, or less than about ten minutes, or less than about five minutes, or less than about four minutes, or less than about three minutes or less than about two minutes, or less than about one minute of performing step (i). In another example, the optical property of the nanoparticle adsorbed with a gliadin molecule is absorbance and the change is absorption at a longer wavelength.

The immunoglobulin that is capable of binding specifically to naturally occurring gliadin may be an anti-gliadin antibody. The anti-gliadin antibody may be any naturally occurring anti-gliadin antibody. For example, the anti-gliadin antibody may be an IgG anti-gliadin antibody or an IgA anti-gliadin antibody.

The methods disclosed herein may be used such that an anti-gliadin antibody, if present in the sample, binds to one or more nanoparticles adsorbed with a gliadin molecule. In one example, binding of an anti-gliadin antibody to the one or more of nanoparticles adsorbed with a gliadin molecule increases aggregation of the nanoparticles adsorbed with a gliadin molecule. For example, naturally occurring anti-gliadin antibodies may be multivalent (e.g., divalent) and may be capable of binding to two or more nanoparticles adsorbed with gliadin, thereby aggregating the nanoparticles. This aggregation may change one or more optical properties of the nanoparticles. Thus, a solution comprising multiple nanoparticles adsorbed with gliadin as disclosed herein may have one or more different optical properties, depending on the extent of aggregation of the nanoparticles, which may in turn depend on the presence of an anti-gliadin antibody in the same solution.

In another example, the present disclosure provides a kit for use in detecting an anti-gliadin antibody in a sample, the kit comprising a nanoparticle adsorbed with a gliadin molecule as disclosed herein, and a buffer. Thus, any embodiment of the nanoparticle adsorbed with a gliadin molecule as disclosed herein may be included in the kit disclosed herein.

As stated above, the present inventors have demonstrated that a nanoparticle adsorbed with a gliadin molecule can be used to perform simple, non-invasive detection methods. Accordingly, in another example, the present disclosure provides a method of diagnosing a gluten-related disorder in an individual, the method comprising (i) contacting a sample of a body fluid obtained from an individual with a nanoparticle adsorbed with a gliadin molecule as disclosed herein, and (ii) detecting an optical property of the nanoparticle adsorbed with a gliadin molecule, wherein a change in the optical property of the nanoparticle adsorbed with a gliadin molecule is indicative of the individual having a gluten-related disorder. In one example, the gluten-related disorder is coeliac disease. In another example, the gluten-related disorder is dermatitis herpetiformis or gluten ataxia.

In another example, the present disclosure provides a kit for use in diagnosing a gluten-related disorder in an individual, the kit comprising a nanoparticle adsorbed with a gliadin molecule as disclosed herein, and a buffer. In another example, the present disclosure provides the use of a nanoparticle adsorbed with a gliadin molecule as disclosed herein, in the manufacture of a diagnostic apparatus for diagnosing a gluten-related disorder. In one example, the gluten-related disorder is a coeliac disease.

In another example, the present disclosure provides the use of a nanoparticle adsorbed with a gliadin molecule as disclosed herein, in the manufacture of an apparatus for detecting an anti-gliadin antibody. The apparatus may be a diagnostic device.

The nanoparticle adsorbed with a gliadin molecule as disclosed herein can be used as a diagnostic agent. In one example, the nanoparticle adsorbed with a gliadin molecule as disclosed herein can be used in diagnosing a gluten-related disorder. Preferably, the gluten-related disorder is a coeliac disease. In another example, the nanoparticle adsorbed with a gliadin molecule as disclosed herein can be used in detecting an anti-gliadin antibody. In another example, the nanoparticle adsorbed with a gliadin molecule as disclosed herein can be used for detecting an anti-gliadin antibody.

The features of any embodiment described herein shall be taken to apply mutatis mutandis to any other embodiment unless specifically stated otherwise.

The present disclosure is not to be limited in scope by the specific embodiments described herein, which are intended for the purpose of exemplification only. Functionally-equivalent products, compositions and methods are clearly within the scope of the invention, as described herein.

BRIEF DESCRIPTION OF DRAWINGS

The present disclosure may be better understood by reference to one or more of the figures, alone or in combination with the detailed description of specific embodiments described herein.

FIG. 2 shows the comparison of the solubilisation of gliadin in cationic surfactant CTAB and in anionic surfactant SDS. When solubilised in SDS, a shift of peaks to the right indicates the formation of large micelles caused by aggregation compared to solubilisation in CTAB, demonstrating the suitability of a cationic surfactant to solubilise gliadin.

KEY TO THE SEQUENCE LISTING

Figure 1:
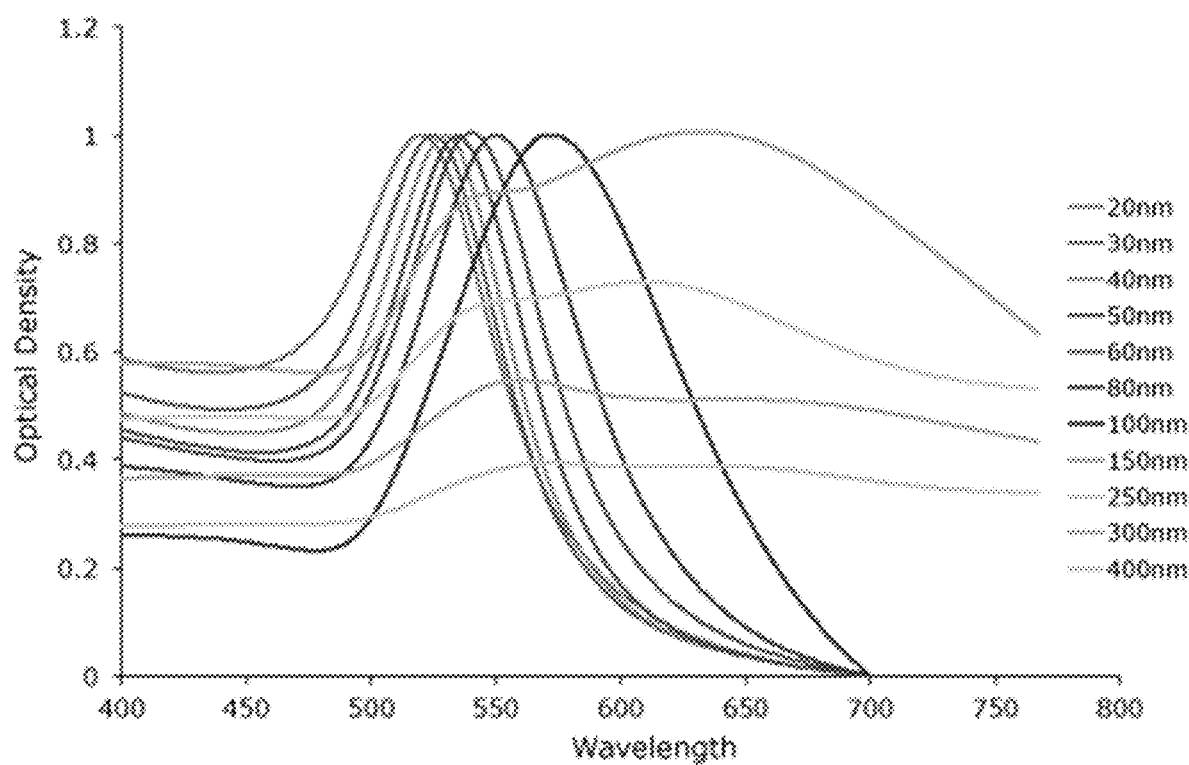
FIG. 1 shows the influence of gold nanoparticle size on the surface plasmon resonance. Absorption maximum (lambda max) increases from 520 nm to 570 nm for gold nanoparticles with sizes from 20 nm to 100 nm.

SEQ ID NO: 1—FASTA sequence for alpha-gliadin protein of *Triticum aestivum*.
SEQ ID NO: 2—FASTA sequence for bovine serum albumin protein of *Bos Taurus*.
SEQ ID NO: 3—FASTA sequence for a gliadin peptide.
SEQ ID NO: 4—FASTA sequence for an alternative gliadin peptide.

DETAILED DESCRIPTION

General Material and Methods

Unless specifically defined otherwise, all technical and scientific terms used herein shall be taken to have the same meaning as commonly understood by one of ordinary skill in the art (e.g., in immunology, nanotechnology, immunohistochemistry, protein chemistry, biochemistry and chemistry).

Throughout this specification, unless specifically stated otherwise or the context requires otherwise, reference to a single step, composition of matter, group of steps or group of compositions of matter shall be taken to encompass one and a plurality (e.g. one or more) of those steps, compositions of matter, groups of steps or group of compositions of matter. For example, "a nanoparticle adsorbed with a gliadin molecule" shall be taken to encompass: a nanoparticle adsorbed with a gliadin molecule; a nanoparticle adsorbed with a plurality of gliadin molecules (e.g., two, three, four, five, six, seven, or more gliadin molecules); a plurality of nanoparticles (e.g., two, three, four, five, six, seven, or more nanoparticles) adsorbed with a gliadin molecule; a plurality of nanoparticles (e.g., two, three, four, five, six, seven, or more nanoparticles) adsorbed with a plurality of gliadin molecules (e.g., two, three, four, five, six, seven, or more gliadin molecules).

The description and definitions of immunoglobulins, antibodies and fragments thereof herein may be further understood by the discussion in Kabat, 1987 and/or 1991, Bork et al., 1994 and/or Chothia and Lesk, 1987 and/or 1989 or Al-Lazikani et al., 1997. The terms "immunoglobulin" and "antibody" as used herein shall be understood to mean all possible variants of immunoglobulins or antibodies known in the art.

The term "and/or", e.g., "X and/or Y" shall be understood to mean either "X and Y" or "X or Y" and shall be taken to provide explicit support for both meanings or for either meaning. As used herein, the term "about", unless stated to the contrary, refers to +/−20%, more preferably +/−10%, of the designated value. For the avoidance of doubt, the term "about" followed by a designated value is to be interpreted as also encompassing the exact designated value itself (for example, "about 10" also encompasses 10 exactly).

As used herein, the terms "linked", "attached", "conjugated", "bound", "coupled", "coated", "covered", "adsorbed" or variations thereof are used broadly to refer to any form of covalent or non-covalent association which joins one entity to another for any period of time.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

Nanoparticles

The nanoparticles disclosed herein can be of any known shape. For example, the nanoparticles may be nanospheres, nanorods, nanowires, nanocubes, nanoplates, or any other shape. For example, the nanoparticles may form the shape of a pyramid, triangle, fractal or any other shape. Preferably, the nanoparticles are nanospheres.

The size of the nanoparticles may be characterized by their diameter. Although the term "diameter" is used normally to refer to the maximal length of a line segment passing through the centre and connecting two points on the periphery of a nanosphere, it is also used herein to refer to the maximal length of a line segment passing through the centre and connecting two points on the periphery of nanoparticles having other shapes, such as nanospheres, nanorods, nanowires, nanocubes, nanoplates, or any other shape.

The diameter of the nanoparticles may be between about 1 nm and about 300 nm. For example, the nanoparticles may have a diameter of between about 1 nm and about 100 nm, such as between about 5 nm and about 80 nm, such as between about 5 nm and about 50 nm, such as between about 5 nm and about 30 nm, such as between about 5 nm and about 25 nm, such as between about 10 nm and about 25 nm, such as between about 15 nm and about 25 nm. In one example, the nanoparticles may have a diameter of between about 1 nm and about 20 nm. In another example, the nanoparticles may have a diameter of between about 5 nm and about 20 nm. In another example, the nanoparticles may have a diameter of between about 20 nm and about 100 nm, such as between about 20 nm and about 80 nm, such as between about 20 nm and about 50 nm, such as between about 20 nm and about 30 nm. In another example, the nanoparticles may have a diameter of less than about 300 nm, such as less than about 100 nm, such as less than about 80 nm, such as less than about 50 nm, such as less than about 40 nm, such as less than about 30 nm, such as less than about 25 nm, such as less than about 20 nm. Preferably, the nanoparticles may have a diameter of about 20 nm. The above measurements may apply to each individual nanoparticle or may apply to the average diameter of all nanoparticles used in any particular instance.

The nanoparticles disclosed herein may be optically and/or magnetically detectable. For example, optical detection may be based on an analysis of the interaction of light with electrons on the nanoparticle surface. At a specific wavelength of light, collective oscillation of electrons on the nanoparticle surface causes a phenomenon called surface plasmon resonance resulting in strong extinction of light (absorption and scattering). The wavelength where detection occurs is dependent on the size of the nanoparticle. FIG. 1 shows the influence of gold nanoparticle size on the surface plasmon resonance. Absorption maximum (lambda max) increases from 520 nm to 570 nm for gold nanoparticles with diameter sizes from 20 nm to 100 nm. Thus, the nanoparticles disclosed herein may be detected optically, such as by analysing their absorption of light.

Intrinsically fluorescent or luminescent nanoparticles, nanoparticles that comprise fluorescent or luminescent moieties, plasmon resonant nanoparticles, and magnetic nanoparticles are among the detectable nanoparticles that can be used. Any method known in the art to be suitable for optically or magnetically detecting the nanoparticles can be used including, but not limited to, spectrometry, fluorescence microscopy, flow cytometry, etc.

The nanoparticles disclosed herein comprise at least a central core. The core may have the dimensions of any nanoparticle disclosed herein. The core may be surrounded by one or more layers of another material. Alternatively or in addition, the nanoparticle may not be surrounded by any layers of another material. Thus, the nanoparticle may consist of, or may consist essentially of, the central core. The core material may comprise or consist of any suitable solid material. For example, the core material may comprise or consist of a synthetic or naturally occurring polymer. Alternatively, the core material may comprise or consist of a metal or a mixture of metals. The metal may be, for example, gold, silver, iron, cobalt, zinc, cadmium, nickel, gadolinium, chromium, copper, manganese, palladium, platinum, tin, aluminium, alloys and/or oxides thereof, or any other metal.

The metal may be any plasmonically active metal or mixtures of metals. In one example, the metal is gold, silver or titanium dioxide. In one particular example, the metal is gold. In another example, the core material may comprise or consist of polymeric silica; in another example, the core material may comprise or consist of graphene; in yet another example, the core material may comprise or consist of a ceramic.

The nanoparticles disclosed herein may be synthesised. Methods for synthesising nanoparticles including, but not limited to citrate-reduction, sodium borohydride-reduction and seeding growth may be used. Thus, the present disclosure provides methods for synthesising nanoparticles. Alternatively, the nanoparticles may be obtained from a number of commercial sources.

The nanoparticles disclosed herein may be functionalised to facilitate binding to a protein (such as a gliadin protein). Any suitable, functionalised nanoparticles can be used.

The nanoparticles disclosed herein may also be stabilised by any means known in the art. In one example, the nanoparticles are stabilised by citrate. Thus, the nanoparticles disclosed herein may be citrate-stabilised nanoparticles. For example, the nanoparticles disclosed herein may be citrate-stabilised gold nanoparticles.

Gliadin Molecules

Any known gliadin molecule obtained from wheat or related grains can be used in the present invention. In one example, the wheat is *Triticum aestivum*. In another example, the wheat or related grains may include: *Triticum spelta* (spelt), *Triticum durum, Triticum dicoccon, Triticum turanicum* or *Triticum monococcum* (einkorn), *Hordeum vulgare* (barley), *Secale* cereal (rye), spelt, *Avena sativa* (oats), *Triticum turgidum* (kamut), einkorn or *Chenopodium quinoa* (quinoa).

The gliadin molecule disclosed herein may be derived from any wheat or related grains as described herein. By 'derived from', it is meant that the molecule may be modified from a naturally occurring gliadin molecule. Thus, the gliadin molecule may retain some similarity in sequence to a naturally occurring gliadin protein or fragment thereof, but may include one or more modifications. The one or more modifications may comprise, for example, one or more amino acid deletions, additions or substitutions. The modifications may improve one or more properties of the gliadin molecule. For example, the modifications may improve the ease with which the gliadin molecule can be adsorbed onto the nanoparticle. The modifications may improve the stability of the molecule's three-dimensional structure.

Protein sequences of gliadin molecules are readily identifiable from publically available databases such as SWISS-PROT. In one example, the gliadin molecule may have an amino acid sequence that is at least 60% identical to SEQ ID NO:1, or a fragment thereof. Thus, the gliadin molecule may have an amino acid sequence that is at least 70%, at least 80%, at least 90%, at least 95%, at least 98%, at least 99%, or that is 100% identical to SEQ ID NO:1, or a fragment thereof.

Gliadin can be elecrophoretically separated into different fractions namely, alpha, beta, gamma, or omega gliadin. Any one or more of these fractions may be used to make the gliadin-adsorbed nanoparticles disclosed herein. Thus, one or more gliadin fraction, or peptide sequences identified from the whole gliadin protein sequence, could be adsorbed on the surface of AuNPs. In one example, a gliadin molecule may comprise or consist of an alpha-gliadin protein, peptide, epitope or a fragment thereof. For example, an alpha-gliadin protein or peptide may be used (Xie et al. *Theor Appl Genet* 121: 1239-1251, 2010). In another example, a gliadin molecule may comprise or consist of a beta-gliadin protein, peptide, epitope or a fragment thereof. For example, a beta-gliadin protein or peptide may be used. In another example, a gliadin molecule may comprise or consist of a gamma-gliadin protein, peptide, epitope or a fragment thereof. For example, a gamma-gliadin protein or peptide may be used. In another example, a gliadin molecule may comprise or consist of an omega-gliadin protein, peptide, epitope or a fragment thereof. For example, an omega-gliadin protein or peptide may be used.

The gliadin proteins, peptides or epitopes disclosed herein may be capable of interacting with antibodies produced by individuals suffering from one or more gluten-related disorders. For example, a peptide or an epitope may comprise or consist of at least 5, at least 6, at least 7, at least 8, at least 9, at least 10, at least 11, at least 12, at least 13, at least 14, at least 15, at least 16, at least 17, at least 18, at least 19 or at least 20 amino acids. In one example, an epitope may comprise or consist of a consecutive sequence of a gliadin molecule. In another example, an epitope may comprise or consist of non-consecutive sequences of a gliadin molecule such that a tertiary structure of a gliadin molecule is formed that retains sufficient conformational similarity to naturally occurring gliadin molecule to be bound by an immunoglobulin that is capable of binding specifically to naturally occurring gliadin molecule. In one example, the gliadin peptide may comprise the sequence QLQPFPQPQLPYPQPQC (SEQ ID NO:3). In another example, the gliadin peptide may comprise the sequence QLQPFPQPQLPYPQPQ (SEQ ID NO: 4). In another example, the gliadin peptide is at least 70%, at least 80%, at least 90%, at least 95%, at least 98%, at least 99%, or 100% identical to QLQPFPQPQLPYPQPQC (SEQ ID NO: 3). In another example, the gliadin peptide is at least 70%, at least 80%, at least 90%, at least 95%, at least 98%, at least 99%, or 100% identical to QLQPFPQPQLPYPQPQ (SEQ ID NO: 4).

The fragments or peptides disclosed herein may be of any length. For example, the fragment may comprise or consist of at least 10, or at least 15, or at least 20, or at least 25, or at least 50, or at least 75, or at least 100, or at least 200 consecutive amino acids of the whole gliadin protein.

In another example, the gliadin molecule may comprise or consist of a gliadin extract. For example, the gliadin extract may be an extract from wheat, barley or rye. Gliadin extracts are well known in the art and are available from a number of commercial sources. In one particular example, the gliadin molecule used is a gliadin extract from wheat.

Anti-Gliadin Antibodies

The anti-gliadin antibodies described herein may be any antibody or fragment thereof capable of specifically binding to gliadin molecules. For example, the anti-gliadin antibodies may be IgG anti-gliadin antibodies. In another example, the anti-gliadin antibodies may be IgA anti-gliadin antibodies. In another example, the anti-gliadin antibodies may be IgE anti-gliadin antibodies. In another example, the anti-gliadin antibodies may be anti-deaminated gliadin peptide (DGP) antibodies. Preferably, the anti-gliadin antibodies are IgG antibodies, since these are prevalent in individuals suffering from gluten-related disorders such as coeliac disease.

Preparation of Nanoparticles Adsorbed with Gliadin Molecules

The nanoparticles described herein may be adsorbed with any suitable gliadin molecules described herein. The method for preparing nanoparticles adsorbed with gliadin molecules may comprise (a) dissolving a gliadin molecule in a solution comprising a cationic surfactant, (b) adding a nanoparticle to the solution obtained in step (a) to form a mixture; and (c) isolating a nanoparticle adsorbed with a gliadin molecule from the mixture obtained in step (b). In one example, the cationic surfactant may be cetyl trimethylammonium bromide. Other cationic surfactants known in the art may alternatively be used. For example, the cationic surfactant may be behentrimonium chloride, benzalkonium chloride, benzethonium chloride, bronidox, cetrimonium chloride, dimethyldioctadecylammonium bromide, dimethyldioctadecylammonium chloride, lauryl methyl gluceth-10 hydroxypropyl dimonium chloride, octenidine dihydrochloride, olaflur, N-oleyl-1,3-propanediamine, stearalkonium chloride, tetramethylammonium hydroxide, thonzonium bromide, or another known cationic surfactant.

Step (a) of the method may further comprise dissolving the gliadin molecule in a solution comprising a cationic surfactant and a polar protic solvent. Any known polar protic solvent may be used. For example, the polar protic solvent may be isopropanol. In another example, the polar protic solvent may be formic acid, n-butanol, nitromethane, ethanol, methanol acetic acid or water.

The polar protic solvent may be combined with the surfactant before the gliadin is added. Alternatively, the gliadin may be added to the cationic surfactant before the polar protic solvent is added. In addition, step (a) may further comprise adding 70% ethanol to the mixture containing the cationic surfactant and polar protic solvent. Thus, for example, step (a) may comprise dissolving the gliadin molecule in a solution comprising a cationic surfactant, a polar protic solvent and 70% ethanol.

The method may also comprise a step of heating the solution obtained in step (a). The solution obtained in step (a) may be heated to about 40° C., or to about 80° C., for example. The solution obtained in step (a) may be heated to a temperature in the range of about 40° C. to about 80° C., such as about 45° C. to about 75° C., such as about 50° C. to about 70° C., such as about 55° C. to about 65° C., such as about 60° C. to about 65° C. Preferably, the solution obtained in step (a) may be heated to a temperature in the range of about 55° C. to about 65° C. In one example, the solution obtained in step (a) may be heated to about 60° C. The heating step (if performed) may be performed for up to about 5 minutes, or up to about 10 minutes, or up to about 15 minutes, or up to about 30 minutes. Alternatively, the heating step (if performed) may be performed for at least about 5 minutes, or at least about 10 minutes, or at least about 15 minutes, or at least about 30 minutes. The heating step (if performed) may be performed for a time between about 5 minutes to about 15 minutes, such as about 5 minutes to about 10 minutes. In one example, the heating step is performed for about 5 minutes.

The method may further comprise filtering the solution obtained in step (a) prior to step (b). Any filter having a pore size capable of allowing solubilised gliadin through the filter may be used. Alternatively, a filter having a pore size capable of retaining solubilised gliadin may be used; followed by reconstitution of the solubilised gliadin. In one example, a filter having a pore size of 0.45 µm may be used.

The method may further comprise a step of incubating the mixture obtained in step (b). The incubation may be from 30 to 90 minutes, such as from 40 to 80 minutes, such as from 50 to 70 minutes, such as for about 60 minutes prior to step (c). In one particular example, the incubation step is performed for about 60 minutes.

The mixture in step (b) may comprise adding the nanoparticles to the solution obtained in step (a) at a ratio (by concentration and/or volume) of about 1:4.1, or to about 1:4.9, for example. The mixture in step (b) may comprise adding the nanoparticle to the solution in step (a) at a ratio in the range of about 1:4.1 to about 1:4.9, such as about 1:4.2 to about 1:4.9, such as about 1:4.3 to about 1:4.8, such as about 1:4.4 to about 1:4.8, such as about 1:4.5 to about 1:4.7. Preferably, the mixture in step (b) may comprise adding the nanoparticles to the solution obtained in step (a) at a ratio of about 1:4.6.

In one example, step (c) comprises centrifugation. In another example, step (c) comprises filtration. Other suitable isolation methods will be apparent to the person skilled in the art.

The nanoparticle described herein may be adsorbed either directly or indirectly with the gliadin molecule. The gliadin molecule may be adsorbed indirectly by a linker. Any suitable linker known in the art may be used. For example, the linker may comprise a protein. The protein may comprise avidin. The linker may comprise another, secondary molecule. The secondary molecule may be, for example, Biotin-PEG-Maleimide. Adsorption via a linker and/or a secondary molecule may be employed particularly when the gliadin molecule is a fragment of gliadin.

Human Serum

"Human serum" as referred to herein may refer to the component of human blood that does not contain blood cells (i.e., serum does not contain white or red blood cells) or clotting factors. Human serum may be considered to be blood plasma without fibrinogens. Accordingly, human serum referred to herein may be obtained from blood plasma after fibrinogen and other clotting factors have been removed.

Thus, human serum as referred to herein may be taken to include all proteins not involved in blood clotting (coagulation), and to include all the electrolytes, antibodies, antigens, hormones, and any exogenous substances (e.g., drugs and microorganisms) normally present in human serum.

Gluten-Related Disorders

The gluten-related disorder referred to herein may be any disorder triggered by ingestion of gluten. Accordingly, the gluten-related disorder which may be diagnosed includes, without limitation, a coeliac disease, dermatitis herpetiformis, gluten ataxia, gluten sensitivity, non-coeliac gluten sensitivity, or other known gluten-related disorders.

Preferably, the gluten-related disorder is an autoimmune condition. For example, the gluten related disorder may be selected from the group consisting of coeliac disease, dermatitis herpetiformis and gluten ataxia.

In one example, the gluten-related disorder is a coeliac disease. Preferably, the coeliac disease may be selected from the group consisting of classical coeliac disease, atypical coeliac disease, latent coeliac disease, and silent coeliac disease. These specific forms of coeliac disease may be collectively referred to herein as "coeliac disease". Thus, the present disclosure relates to methods and kits for diagnosing coeliac disease.

Detection Methods

The nanoparticles adsorbed with gliadin molecules disclosed herein have been shown to be capable of specifically binding to anti-gliadin antibodies. Thus, the present disclosure provides a method of detecting anti-gliadin antibodies in a sample. The method may comprise (i) contacting a sample of a body fluid obtained from an individual with a nanoparticle adsorbed with a gliadin molecule as disclosed herein, and (ii) detecting an optical property of the nanoparticle adsorbed with a gliadin molecule, wherein a change in the optical property of the nanoparticle adsorbed with a gliadin molecule is indicative of the presence of anti-gliadin antibodies in the sample. Thus, the methods disclosed herein may comprise a step of detecting an optical property of the nanoparticle adsorbed with a gliadin molecule before contact with the sample and after contact with the sample. Alternatively, it will be appreciated that a single detection step may be performed after contact with the sample and any change in the optical property may be determined by comparison to a predetermined reference level of that optical property in the absence of the sample.

Optical properties of the nanoparticles adsorbed with gliadin molecules as disclosed herein include, but are not limited to colour, absorbance properties, solubility or fluorescence properties. For example, the optical property of the nanoparticle adsorbed with a gliadin molecule may be absorbance. Absorbance may be detected in the ultraviolet-visible absorption spectrum or the visible absorption spectrum.

The change in the optical property that is indicative of the presence of anti-gliadin antibodies in the sample may be an increase or a decrease in the optical property. For example, the change in absorbance may be an increase in the absorbance wavelength. Alternatively, the change in absorbance may be a decrease in the absorbance wavelength. The change in optical property may be measured using any suitable instrument capable of detecting a change in any of the optical properties disclosed herein. Alternatively, the change in optical property may be detected visually by the human eye. For example, a change in absorbance may be accompanied by a change in colour (e.g., from red to colourless), which may be detected by eye. The change in the optical property may be detected within less than about thirty minutes, or less than about ten minutes, or less than about five minutes, or less than about four minutes, or less than about three minutes or less than about two minutes, or less than about one minute of the gliadin-adsorbed nanoparticles being contacted with the sample being tested.

The change in optical property detected in any of the methods disclosed herein may be indicative of a change in solubility of the nanoparticle adsorbed with gliadin molecules upon contact with a sample containing anti-gliadin antibodies. Such a change in solubility may be an increase in agglutination or aggregation, with the result being precipitation. The change in solubility may be measured using any suitable instrument capable of detecting a change in solubility disclosed herein. Alternatively, the change in solubility may be detected visually by the human eye. For example, the formation of a precipitate may be detected by eye. The formation of the precipitate may be detected within less than about ten minutes, or less than about five minutes, or less than about four minutes, or less than about three minutes or less than about two minutes, or less than about one minute.

The detection methods disclosed herein may be performed on a sample previously taken from an individual. The sample may comprise a body fluid. The body fluid may be selected from the group consisting of saliva, blood, urine or a gastrointestinal secretion. Preferably, the body fluid is saliva.

The detection methods disclosed herein may be performed on a sample from any individual having or suspected of having a gluten-related disorder such as coeliac disease. In one example, the detection methods disclosed herein may be performed on an individual having an IgA deficiency. Thus, the detection methods disclosed herein may comprise a step of selecting a sample from an IgA deficient individual for analysis. The individual's IgA deficiency may be predetermined. Alternatively, the detection methods disclosed herein may comprise determining whether an individual is IgA deficient and selecting a sample from the individual for analysis using the detection method disclosed herein if that individual is IgA deficient. It is estimated that 10-15% of individuals suffering from coeliac disease are IgA deficient.

Diagnostic Methods

As indicated above, the nanoparticles adsorbed with gliadin molecules disclosed herein have been shown to be capable of specifically binding to anti-gliadin antibodies. Thus, the present disclosure also provides a method of diagnosing a gluten-related disorder in an individual, the method comprising (i) contacting a sample of a body fluid obtained from an individual with a nanoparticle adsorbed with a gliadin molecule as disclosed herein, and (ii) detecting an optical property of the nanoparticle adsorbed with a gliadin molecule, wherein a change in the optical property of the nanoparticle adsorbed with a gliadin molecule is indicative of the individual having a gluten-related disorder. Thus, the diagnostic methods disclosed herein may comprise a step of detecting an optical property of the nanoparticle adsorbed with a gliadin molecule before contact with the sample and after contact with the sample. Alternatively, it will be appreciated that a single detection step may be performed after contact with the sample and any change in the optical property may be determined by comparison to a predetermined reference level of that optical property in the absence of the sample.

The diagnostic methods disclosed herein may comprise any of the features of the detection methods disclosed herein. Thus, the optical properties of the nanoparticles adsorbed with gliadin molecules which may be detected in the diagnostic methods disclosed herein include, but are not limited to colour, absorbance properties, solubility or fluorescence properties. For example, the optical property of the nanoparticle adsorbed with a gliadin molecule may be absorbance. Absorbance may be detected in the ultraviolet-visible absorption spectrum or the visible absorption spectrum.

The change in the optical property that is indicative of the individual having a gluten-related disorder may be an increase or a decrease in the optical property. For example, the change in absorbance may be an increase in the absorbance wavelength. Alternatively, the change in absorbance may be a decrease in the absorbance wavelength. The change in optical property may be measured using any suitable instrument capable of detecting a change in any of the optical properties disclosed herein. Alternatively, the change in optical property may be detected visually by the human eye. For example, a change in absorbance may be accompanied by a change in colour (e.g., from red to colourless), which may be detected by eye. The change in the optical property may be detected within less than about thirty minutes, or less than about ten minutes, or less than about five minutes, or less than about four minutes, or less than about three minutes or less than about two minutes, or less than about one minute of the gliadin-adsorbed nanoparticles being contacted with the sample being tested.

The change in optical property that is indicative of the individual having a gluten-related disorder may be indicative of a change in solubility of the nanoparticle adsorbed with gliadin molecules upon contact with a sample. Such a change in solubility may be an increase in agglutination or aggregation, with the result being precipitation. The change in solubility may be measured using any suitable instrument capable of detecting a change in solubility disclosed herein. Alternatively, the change in solubility may be detected visually by the human eye. For example, the formation of a precipitate may be detected by eye. The formation of the precipitate may be detected within less than about thirty minutes, or less than about ten minutes, or less than about five minutes, or less than about four minutes, or less than about three minutes or less than about two minutes, or less than about one minute.

The diagnostic methods disclosed herein may be performed on an individual in situ, or on a sample previously taken from an individual. Preferably, the methods are performed on a sample taken from the individual. The sample may comprise a body fluid. The body fluid may be selected from the group consisting of saliva, blood, urine or a gastrointestinal secretion. Preferably, the body fluid is saliva.

The diagnostic methods disclosed herein may be performed on any individual having or suspected of having a gluten-related disorder such as coeliac disease. In one example, the diagnostic methods disclosed herein may be performed on an individual having an IgA deficiency. Thus, the diagnostic methods disclosed herein may comprise a step of selecting an IgA deficient individual for analysis. The individual's IgA deficiency may be predetermined. Alternatively, the methods disclosed herein may comprise determining whether an individual is IgA deficient and selecting the individual for diagnosis using the diagnostic method disclosed herein if that individual is IgA deficient. It is estimated that 10-15% of individuals suffering from coeliac disease are IgA deficient.

Sample Pre-Treatment

In any of the detection methods or diagnostic methods disclosed herein, a sample containing or suspected of containing anti-gliadin antibodies may optionally be pre-treated prior to reaction with nanoparticles adsorbed with gliadin molecules. For example, pre-treatment of a sample may comprise diluting the sample in a suitable buffer. The dilution may be performed in order to ensure that the antibody is present at a concentration known to be suitable for detection by means of the detection methods, diagnostic methods or kits described herein. In another example, pre-treatment of the sample may comprise concentrating a diluted sample. The final concentration of the anti-gliadin antibody in the sample may be provided in a range of about 2 µg/mL to about 10 µg/mL. In one example, the anti-gliadin antibody in the sample has a final concentration of about 4 µg/mL to about 10 µg/mL. In yet another example, the anti-gliadin antibody in the sample has a final concentration of about 6 µg/mL to about 10 µg/mL. In yet another example, the anti-gliadin antibody in the sample has a final concentration of about 7 µg/mL to about 9 µg/mL. Preferably, the anti-gliadin antibody in the sample has a final concentration of about 8 µg/mL. Suitable methods for ensuring that the anti-gliadin antibodies are provided in the sample to be tested within these ranges of concentrations will be known to a person skilled in the art.

When the sample is a serum sample (such as a human serum sample), the sample may be diluted in a suitable buffer at a ratio of sample:buffer (by volume) from about 1:10 to about 1:1000, such as from about 1:10 to about 1:500, such as about 1:10 to about 1:100, such as from about 1:10 to about 1:50. In a preferred example, the sample is diluted in a buffer in a ratio of sample:buffer of about 1:50. Any suitable buffer may be used. In one example, the buffer used for the dilution is a HEPES buffer.

A mixture comprising a sample containing or suspected of containing anti-gliadin antibodies may optionally be pre-treated with a detergent prior to reaction with nanoparticles adsorbed with gliadin. The addition of a detergent may be performed on any sample described herein, though is particularly useful when the sample comprises serum (e.g., when the sample is a human serum sample). As used herein, the term "detergent" is intended to refer to any compound that is amphipathic in nature. For example, the detergent may contain a polar group at one end and long hydrophobic carbon chain at the other end. The detergent as disclosed herein may be a biological detergent. The biological detergent used herein may inhibit background absorbance measurements in immunoassays for example, enzyme-linked immunosorbent assays (ELISA) and Western blotting. Biological detergents are commonly used to disrupt the bipolar lipid membrane of cells in order to release and solubilize membrane-bound proteins. Some detergents can be used to solubilize recombinant proteins, while others are recommended for the stabilization, crystallization, or denaturation of proteins. Detergents can align at aqueous/non-aqueous interfaces, resulting in reduced surface tension, increased miscibility, and stabilization of emulsions.

In one example, the biological detergent may be an ionic detergent. The ionic detergent may include, for example; cetyltrimethylammonium bromide, chenodeoxycholic acid free acid, chenodeoxycholic acid sodium salt, cholic acid sodium salt, cholic acid sodium salt ULTROL® Grade, deoxycholic acid sodium salt, deoxycholic acid sodium salt ULTROL® Grade, glycocholic acid sodium salt, glycodeoxycholic acid sodium salt, glycolithocholic acid sodium salt, glycoursodeoxycholic acid sodium salt, lauroylsarcosine sodium salt, LPD-12, Sodium n-Dodecyl Sulfate, sodium n-dodecyl sulfate high purity, sodium n-dodecyl sulfate molecular biology grade, sodium n-dodecyl sulfate 20% solution (w/v), taurochenodeoxycholic acid sodium salt, taurocholic acid sodium salt, taurocholic Acid, sodium salt ULTROL® Grade, taurodeoxycholic acid sodium salt, tauroursodeoxycholic acid sodium salt and ursodeoxycholic acid sodium salt.

In another example, the detergent may be a non-ionic detergent. For example, the non-ionic detergent may include: APO-10, APO-12, Big CHAP, Big CHAP Deoxy, BRIJ® 35 Detergent 30% Aqueous Solution, BRIJ® 35 Detergent PROTEIN GRADE®, 10% Solution, Sterile-Filtered, C12E8, C12E8 PROTEIN GRADE® Detergent 10% Solution, C12E9 PROTEIN GRADE® Detergent 10% Solution, Cyclohexyl-n-hexyl-b-D-maltoside, ULTROL® Grade, n-Decanoylsucrose, n-Decyl-b-D-maltopyranoside, ULTROL® Grade, Digitonin Alcohol-Soluble High Purity, Digitonin High Purity, n-Dodecanoylsucrose, n-Dodecyl-b-D-glucopyranoside, n-Dodecyl-b-D-maltoside, ULTROL® Grade, ELUGENT™ Detergent 50% Solution, GENAPOL® C-100 PROTEIN GRADE® Detergent 10% Solution SterileFiltered, GENAPOL® X-080 PROTEIN GRADE® Detergent 10% Solution SterileFiltered, GENAPOL® X-100 PROTEIN GRADE® Detergent 10% Solution SterileFiltered, HECAMEG, n-Heptyl-b-D-glucopyranoside, n-Heptyl-b-D-thioglucopyranoside ULTROL® Grade 10% Solution, n-Hexyl-b-D-glucopyranoside, MEGA-8 ULTROL® Grade, MEGA-9 ULTROL® Grade, MEGA-10 ULTROL® Grade, n-Nonyl-b-D-glucopyranoside, NP-40 Alternative, NP-40 Alternative PROTEIN GRADE® Detergent 10% Solution Sterile-Filtered, n-Octanoylsucrose, n-Octyl-b-D-glucopyranoside, n-Octyl-b-D-glucopyranoside ULTROL® Grade, n-Octyl-b-D-maltopyranoside, n-Octyl-b-D-thioglucopyranoside ULTROL® Grade, PLURONIC® F-127 PROTEIN GRADE® Detergent 10% Solution Sterile-Filtered, Saponin, TRITON® X-100 Detergent, TRITON® X-100

PROTEIN GRADE® Detergent 10% Solution Sterile-Filtered, TRITON® X-100 Detergent Molecular Biology Grade, TRITON® X-100 Detergent Hydrogenated, TRITON® X-100 Hydrogenated PROTEIN GRADE® Detergent 10% Solution SterileFiltered, TRITON® X-114 PROTEIN GRADE® Detergent 10% Solution Sterile-Filtered, TWEEN® 20 Detergent, TWEEN® 20 Detergent Molecular Biology Grade, TWEEN® 20 PROTEIN GRADE® Detergent 10% Solution Sterile-Filtered and TWEEN® 80 PROTEIN GRADE® Detergent 10% Solution Sterile-Filtered.

In another example, the detergent may be a zwitterionic detergent. Such detergents include, for example: ASB-C7BzO, ASB-14, ASB-14-4, ASB-16, ASB-C6Ø, ASB-C8Ø, CHAPS, CHAPSO, DDMAB, DDMAU, EMPIGEN® BB Detergent 30% Solution, PMAL-B-100, ZWITTERGENT® 3-08 Detergent, ZWITTERGENT® 3-10 Detergent, ZWITTERGENT® 3-12 Detergent, ZWITTERGENT® 3-14 Detergent and ZWITTERGENT® 3-16 Detergent.

Preferably, the detergent is a non-ionic detergent. Preferably, the non-ionic detergent is Tween20.

Kits

The nanoparticles adsorbed with gliadin molecules may be provided in the form of a kit. In one example, a kit may comprise the nanoparticles adsorbed with gliadin molecules of the disclosure and instructions for use. The instructions for use may provide directions for determining whether or not an individual has a gluten-related disorder in accordance with a method of the present disclosure. Alternatively, or in addition, a kit may comprise an apparatus for detecting a change in an optical property of the nanoparticles adsorbed with gliadin molecules. For example, the apparatus may be a lateral flow device, dipstick, tube, coated plate (such as a 12-well, 48-well, 96-well plate or similar), glass slide, microfluidic apparatus or other solid surface.

The kit may comprise a standard comparison chart or card or software application, and detecting a change in an optical property of the nanoparticles adsorbed with gliadin molecules may comprise comparing the colour of the nanoparticles adsorbed with gliadin molecules after contact with a sample of a body fluid obtained from an individual, wherein the standard comparison chart or card or software application assists the user in identifying the result of the diagnostic test. The standard comparison chart or card or software application may comprise a reference level predetermined from a set of samples known to have a given concentration of anti-gliadin antibodies, which may have been taken from known sufferers of a gluten-related disorder or may be indicative of such anti-gliadin antibody concentrations in the body fluid of known sufferers of a gluten-related disorder. By matching the colour of the nanoparticles adsorbed with gliadin molecules after contact with a sample of a body fluid obtained from an individual, a value or result may be obtained and such result may simply be observed or electronically recorded in some manner (such as via a smartphone). For example, this value or result may indicate that the individual has a gluten-related disorder.

The kit may comprise a device that is suitable for point of care testing. Thus the kit may comprise a hand held device to allow the portable testing of a sample.

The present disclosure is now described further in the following non-limiting examples.

Example 1: Materials and Methods

Materials 20 nm citrate stabilised gold nanoparticles (catalogue number 741965) were obtained from Sigma-Aldrich. 100 g of the protein gliadin (catalogue number G3375), 100 g of bovine serum albumin (BSA; catalogue number A2153), anti-gliadin antibody from rabbit (catalogue number G9144), and IgG antibody from whole rabbit serum (catalogue number 15006) were also obtained from Sigma-Aldrich. Water supplied from a MilliQ water purifier was used throughout.

Gliadin Solubilisation in Solvents

Solubility of gliadin was first tested using a variety of solvents including non-polar, polar aprotic and polar protic sovents. Particular solvents used included acetone (polar aprotic), chloroform (non-polar), dimethylsulphoxide (DMSO; polar aprotic), dimethylformamide (DMF; polar aprotic) and methanol (polar protic). 1 mg of gliadin (Sigma-Aldrich) was dissolved in these solvents by adding and stirring.

Next, solubility of gliadin was tested using a solvent combination comprising a polar aprotic solvent and a non-polar solvent. 1 mg of gliadin was dissolved in a mixture comprising a combination of polar aprotic solvent (250 µL of acetone) and non-polar solvent (250 µL of chloroform).

Next, solubility of gliadin was tested using a combination of a polar protic solvent with a non-polar solvent. 1 mg of gliadin was dissolved in a mixture comprising a combination of a polar protic solvent, (500 µL of methanol) and a non-polar solvent (500 µL dichloromethane (DCM)).

Next, solubility of gliadin was tested using a combination of two polar protic solvents. Isopropanol (IPA) and ethanol were used as exemplary polar protic solvents.

Subsequently, a three-step protocol for gliadin solubilisation was designed comprising a surfactant, a polar protic solvent and heating.

Surfactant and Polar Protic Solvent

To compare the colloidal stability of gliadin in different surfactants, two samples were prepared. Firstly, 1 mg of gliadin was dissolved in 500 µL of 10 mM cetyl trimethylammonium bromide (CTAB) in water and 500 µL of isopropyl alcohol (IPA). Secondly, 1 mg of gliadin was dissolved in 500 µL of 10 mM Sodium dodecylsulphate (SDS) in water and 500 µL of IPA. The final targeted gliadin concentration was 1 µg/mL.

Heating 1 mg of gliadin was added to 500 µL of 10 mM Cetyl ammonium bromide (CTAB) in water and 500 µL of Isopropyl alcohol (IPA). This mixture was heated at different temperatures (20° C., 40° C., 60° C. and 80° C.) for 5 minutes in order to assess the effect of heating on gliadin solubility.

Protocol for Solubilisation of Gliadin

Having determined suitable examples of surfactant, polar aprotic solvent and temperatures for optimal solubilisation of gliadin, the inventors devised the following solubilisation protocol.

To solubilise gliadin, 5 mg of gliadin was weighed and dissolved in 2500 µL of 10 mM aqueous Cetyl Trimethylammonium Bromide (CTAB) solution in 15 mL Falcon™ Conical Centrifuge tubes. The gliadin was then heated for 5 minutes at 60° C. and vortexed for 5 minutes. 2500 µL of 100% isopropanol was added to the tube and vortexed again for 1 minute in order to completely dissolve gliadin. The dissolved gliadin was then filtered using a Ministart® non-pyrogenic filter unit with a pore size of 0.45 µm. The filtered gliadin was then used for adsorption to 20 nm gold nanoparticles in citrate solution.

Preparation of Nanoparticles Adsorbed with Gliadin Molecules (Gliadin-AuNPs)

To adsorb gold nanoparticles with gliadin, 600 μL of 20 nm gold nanoparticles in citrate solution were added dropwise to the side of Falcon™ Conical Centrifuge tubes each containing 2800 μL of the filtered flow through of gliadin dissolved in 10 mM aqueous CTAB and isopropanol as described above. The tubes were incubated at room temperature for 60 minutes and were vortexed for 30 seconds every 10 minutes. The solution was centrifuged at 4500 g for 30 minutes using an Eppendorf® Microcentrifuge. The supernatant was discarded and the pellet was re-dispersed in 150 μL of MilliQ water. The 20 nm AuNPs adsorbed with gliadin prepared by this protocol were 2× concentrated and used as a standard concentration for all immunoassays. These samples were stored at 4° C. until further use.

As a control, nanoparticles adsorbed with bovine serum albumin were prepared. 50 μL of 20 nm AuNPs in citrate solution was transferred to an Eppendorf tube. 500 μL of 10 μg/mL BSA dissolved in 10 mM HEPES was added to 50 μL of AuNPs while vortexing. The tubes were incubated for 30 minutes at room temperature while stirring. The solution was centrifuged for 30 minutes at 4500 g. The pellet was resuspended in 500 μL MilliQ water and centrifuged at 4500 g for 30 minutes using Eppendorf® Microcentrifuge. The supernatant was discarded and the pellet was again suspended in 500 μL HEPES buffer followed by centrifugation at 4500 g for 30 minutes using an Eppendorf® Microcentrifuge. The AuNP-BSA conjugate peaks were observed using Zetasizer Nanosystem (Malvern) and stored at 4° C. until further use.

Calculation of the Molar Extinction Coefficient of Gliadin and BSA

Molar extinction coefficient, also known as molar absorption coefficient, of a particular protein is the absorbance of the protein at the ultraviolet wavelength of 280 nm. Absorption of a protein at 280 nm is related to its amino acids that contain aromatic rings, for example, amino acids tryptophan (Trp, W), tyrosine (Tyr, Y) and to a lesser extent amino acid cysteine (Cys, C). The molar extinction coefficient of a particular protein can be calculated from its protein sequence. Calculation is performed based on the weighted sum of the 280 nm molar absorption coefficients of these three constituent amino acids, as described in the following equation (Gill et al. Anal. Biochem. 182:319-26, 1989 and Pace et al Protein Sci. 4:2411-23, 1995):

$$\varepsilon = (nW \times 5500) + (nY \times 1490) + (nC \times 125)$$

where n is the number of each residue and the stated values are the amino acid molar absorptivities at 280 nm.

The ProtParam tool (ExPasy Bioinformatics Resource Portal) was used to compute the molar extinction coefficient of proteins gliadin and BSA. Gliadin was specified as Swiss-Prot accession number (P02863). The computation was carried out on the complete sequence of gliadin composed of 286 amino acids. BSA is specified as Swiss-Prot accession number (P02769). The extinction coefficient was calculated on the complete sequence composed of 607 amino acids. The results of the analysis are described in Table 1.

TABLE 1

Molecular extinction coefficient of gliadin and protein sequence

| Protein | Molecular weight | Extinction coefficient |
|---|---|---|
| Gliadin | 31 kDa | 19285 $M^{-1}cm^{-1}$ |
| BSA | 66.5 kDa | 47790 $M^{-1}cm^{-1}$ |

Determination of Concentration of Gliadin or BSA Adsorbed to the AuNPs

Nanodrop (ND-1000 Nanodrop Technologies, Inc.) was performed on the AuNPs adsorbed with gliadin or BSA to check for concentration and purity. As gliadin was dissolved in a cationic surfactant (CTAB) followed by a polar aprotic solvent (isopropanol) different controls were used to determine the background absorbance due to these solvents. The concentration of the sample based on the spectral measurement was determined by the in-built Nanodrop ND software with regard to the extinction coefficients calculated above.

Characterization of AuNPs by Dynamic Light Scattering (DLS)

The nanoparticle diameters can be measured using dynamic light scattering (DLS) (NanoSizer, Malvern technologies, Inc.), which is based on Brownian motion and measures the intensity fluctuations of the light diffused by nanoparticles in a medium. The instrument was equipped with a 633 nm laser; measurements were carried out at 25° C. in disposable cuvettes using a sample volume of 500 μL and detected using a 173° back scattering detector. Each sample was measured in duplicate and the mean value reported. Each measurement consisted of 3 runs over 2 minutes each and each sample was measured in duplicate and the mean value reported.

Transmission Electron Microscopy

Transmission electron microscopy (TEM) micrographs were recorded with a 200 kV FEI electron microscope fitted with a Gatan (Pleasantville, Calif.) CCD camera. Samples were prepared by placing 2 μL of AuNP adsorbed with gliadin onto a carbon-coated TEM copper grid (300 mesh, ProSciTech) and the sample allowed to air dry for 15 minutes.

UV-Vis Measurements

UV-Vis measurements were carried out using a Cary Series UV-Vis spectrophotometer (Agilent Technologies) using a standard 1 cm path-length quartz cuvette. Spectra were obtained from 200 nm to 800 nm. MilliQ water was used as the blank (control). Readings were taken in duplicate and the student's t-test was used to determine the p value.

Analysis of the Interaction of Gliadin-AuNP with Anti-Gliadin Antibody and Non-Specific IgG Antibody The general immunoassay format used to assess the activity of AuNPs adsorbed with gliadin with the antibodies is outlined below. Assay steps were performed at room temperature. Briefly, 200 μL of AuNPs adsorbed with gliadin were added to 1.5 mL low protein binding Eppendorf® tubes. Anti-gliadin antibody from rabbit (Sigma-Aldrich) was added to each of the tubes in concentrations ranging from 2 μg/mL to 10 μg/mL. To determine the specificity of the reaction between gliadin adsorbed AuNPs and anti-gliadin antibody, IgG from rabbit serum (Sigma-Aldrich) was used as a control and added to 200 μL AuNPs adsorbed with gliadin in concentrations ranging from 2 μg/mL to 10 μg/mL MilliQ water was added to the tubes to bring the final volume in each Eppendorf tube to 500 μL.

In another control experiment, 200 μL of AuNPs adsorbed with BSA were added to 1.5 mL low protein binding Eppendorf® tubes. Anti-gliadin antibody from rabbit was added to each of the tubes in concentrations ranging from 2 µg/mL to 10 µg/mL to compare the specificity of the reaction between BSA adsorbed AuNPs with the gliadin adsorbed AuNPs.

Analysis of the interaction of gliadin-AuNPs with anti-gliadin antibodies in human saliva Human saliva samples spiked with anti-gliadin antibodies at various dilutions comparable to that seen in coeliac patients were prepared. Approximately 300 µL of normal human saliva was spiked with anti-gliadin antibody at various dilutions comparable to that seen in coeliac patients, and was added to 200 µL 20 nm AuNPs adsorbed with gliadin, gently mixed and was allowed to incubate for 30 minutes. 500 µL of the sample was used for UV-Vis analysis. At least three independent experiments were conducted for each assay.

Analysis of the Interaction of Gliadin-AuNPs with Anti-Gliadin Antibodies in Human Serum The general immunoassay format used to assess the activity of AuNPs adsorbed with gliadin with anti-gliadin antibodies is outlined below. Assay steps were performed at room temperature.

Briefly, human serum was diluted to 1:50 using 10 mM HEPES Buffer. 300 µL of diluted serum was added to 200 µL of AuNPs adsorbed with gliadin in 2 mL low protein binding tubes (Eppendorf). 10 µL of 0.1% Tween20 (Sigma-Aldrich) in 10 mM HEPES buffer was added to the tubes containing serum and AuNPs adsorbed with gliadin. The tubes were incubated for 60 minutes at room temperature. Anti-gliadin antibody at a concentration of 4 μg/mL from rabbit (Sigma-Aldrich) was added to tube A. In control tube B, buffer was added instead of anti-gliadin antibody. The tubes were gently mixed and incubated for 30 minutes. Visual observation was made for any precipitate formation and/or colour change.

Example 2: Alpha-Gliadin from *Triticum aestivum*

The inventors set out to determine the type of gliadin (alpha, beta, gamma, or omega) to investigate and also to determine which organism from which the gliadin protein would be investigated (Lock et al. *Clin Exp Immunol* 116: 258-262, 1999).

Alpha type gliadin with an average molecular weight of 31 kDa was chosen as it is the most common form of gliadin found in nature and represents 15-30% of the total proteins in wheat grain (Wang et al. *Agric Sci China* 6:25-32, 2007). Additionally, alpha gliadins are also commonly found in patients suffering from coeliac disease (Anderson et al. *Nature Medicine* 6:337-342, 2000). The ability of gliadin protein to trigger coeliac disease can be understood from its structural features. The protein contains a unique structural domain; the repetitive domain, that contains an elevated content of amino acids glutamine and proline that are arranged in a repetitive pattern. In addition, gliadin also contains six cysteine residues that form three intramolecular bonds resulting in a globular structure. Initial studies have shown that the intact three-dimensional structure of gliadin is not necessary for triggering coeliac disease and a transition from α-helix to a more relaxed open coiled conformation is necessary for gliadin to become immunogenic (Weiser et al. *Acta Paediatrica,* 412:3-9, 1996).

It will be understood that the term "gliadin" as used herein includes "alpha-gliadin". As gliadin is a component of gluten from wheat, the inventors performed a search on the publically available NCBI database and selected a suitable gliadin protein sequence from the common wheat *Triticum aestivum* (Genbank entry: ABQ52128:1) (SEQ ID NO: 1).

Example 3: Solubility of Gliadin

The inventors set out to determine the solubility of gliadin amongst a wide variety of solvents. Gliadin is a hydrophobic protein and its solubility was first tested in a variety of non polar, protic and aprotic solvents as described above. These solvents include acetone, chloroform, dimethylsulphoxide (DMSO), dimethylformamide (DMF) and methanol.

Of all the polar aprotic solvents listed, no solubility was observed (solubility was determined by visual inspection). Partial solubility was achieved using a solvent mixture of a polar protic solvent (methanol) and a non-polar solvent (dichloromethane).

No solubilisation of gliadin was observed when using a combination of a polar aprotic solvent such as acetone together with a non-polar solvent such as chloroform.

Partial solubility of gliadin was observed using a solvent combination comprising of a polar protic solvent such as methanol with a non-polar solvent such as DCM.

High solubility was achieved suing a combination of two polar protic solvents, for example, comprising isopropanol (IPA) and 70% ethanol.

During validation experiments of protein solubilisation, gliadin could be solubilised (in the presence of CTAB) in IPA alone, or in 70% ethanol alone. The use of 70% ethanol alone was later discontinued as ethanol caused flocculation of the AuNPs. This led to a decrease in the ability of AuNPs to adsorb gliadin.

The inventors then sought to achieve high solubilisation of gliadin by unfolding the globular structure of the protein. To do this, the inventors devised a three step protocol comprising; (i) use of a surfactant (ii) the use of a polar protic solvent and (iii) a heating step.

In step (i) of the protein solubilisation protocol, the inventors sought to investigate if the use of a surfactant would help in dissolving the gliadin protein by decreasing the surface tension between the protein and water. Given the structure of gliadin, an anionic surfactant such as sodium dodecyl sulphate (SDS) and a cationic surfactant such as cetyl trimethylammonium bromide (CTAB) were chosen as possible surfactants that could interact with the protein by forming smaller micelles and help in solubilisation of the protein. It was observed that at the same concentration (10 mM), while SDS caused the protein aggregation, CTAB surfactant formed small micelles by forming electrostatic and hydrophobic interactions with gliadin and helped in solubilising the protein (FIG. 2). In particular, size distribution by volume for gliadin indicated the formation of small micelles (between 90 nm and 417 nm) when dissolved in CTAB, whereas in the presence of SDS, large micelles (between 90 nm and 750 nm) were formed that resulted in protein aggregation. From this, the inventors determined that a cationic surfactant (for example, CTAB, though others may also be used) was particularly beneficial in the solubilisation of gliadin.

In step (ii) of the solubilisation protocol, the inventors sought to determine if a polar protic solvent such as isopropyl alcohol (IPA) could be used. This was based on the theory that IPA could act as a diluent for gliadin by entering the interfacial area of the protein, pulling apart the surfactant molecules and in the process, improve gliadin solubilisation. As shown in Table 2, it was found that IPA with surfactant CTAB, does improve the solubility of gliadin.

In step (iii) of the solubilisation protocol, the inventors investigated if the effect of heating helps in the solubilisation of 1 mg/ml of gliadin in a mixture comprising the surfactant CTAB and the polar aprotic solvent IPA. Heating was performed at a temperature range of 20° C. to 80° C. for 5 minutes. Protein concentration was measured after the heating step using the NanoDrop. Results are provided in Table 2 and FIG. 3.

TABLE 2

Average protein concentration (mg/mL) of gliadin at different temperatures (° C.)

| Temperature (° C.) | Average protein concentration (mg/mL) |
|---|---|
| 20 | 0.55 |
| 40 | 0.62 |
| 60 | 0.73 |
| 80 | 0.52 |

TABLE 3

Average protein concentration (mg/mL) of gliadin in samples with and without the addition of IPA

| Sample | Average Protein Concentration (mg/mL) |
|---|---|
| Gliadin/CTAB/IPA/60° C. | 0.73 |
| Gliadin/CTAB/60° C. | 0.57 |

Figure 3:
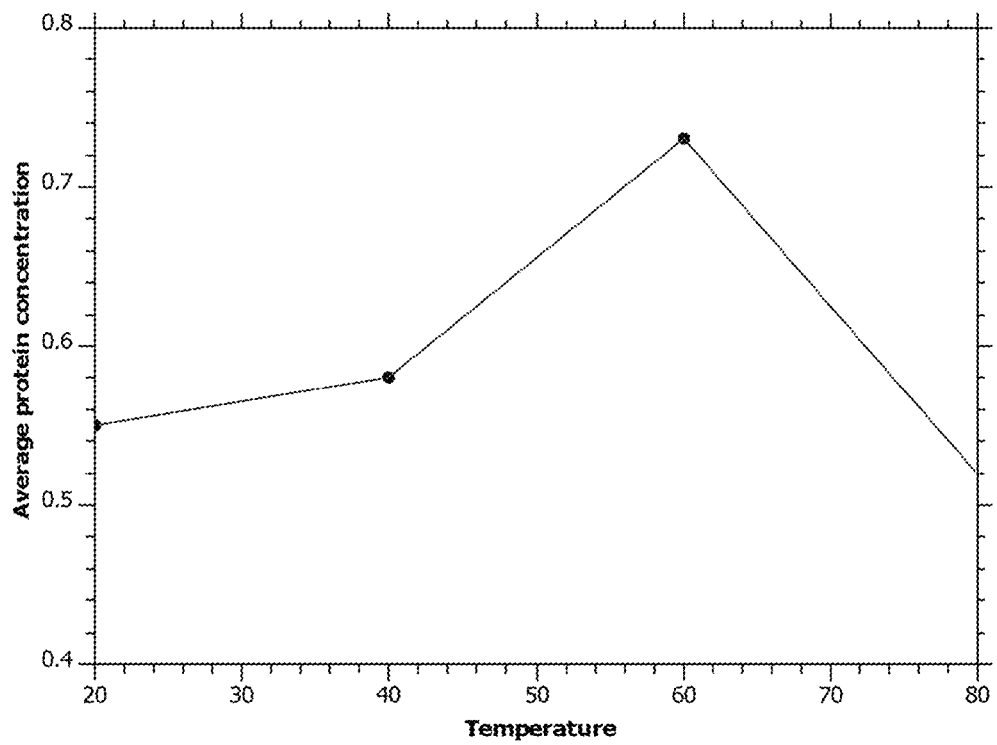
FIG. 3 shows the average protein concentration (mg/mL) of gliadin at different temperature points such as 20° C., 40° C., 60° C. and 80° C.

As illustrated in FIG. 3, the inventors found that the soluble gliadin concentration reached a maximum at 60° C., indicating an increase in protein solubilisation. Without wishing to be bound by theory, the increase in protein concentration at 60° C. may be caused by a linear decrease in hydrogen bonds and electrostatic bonds within the gliadin protein.

As shown in Table 2, when the heating temperature was increased above 60° C., a decrease in protein concentration was observed. Without wishing to be bound by theory, this decrease in protein concentration may be caused by the protein undergoing denaturation, which may involve a helix-coil transition. This may also result in exposure of the immunogenic epitopes of gliadin that are responsible for triggering coeliac disease.

Example 4: Adsorption of Gliadin on the Surface of Gold Nanoparticles (AuNPs)

The inventors sought to determine suitable conditions to adsorb gliadin on to the surface of AuNPs.

Incubation Period of Gliadin with AuNP

The inventors sought to determine suitable time periods for incubating soluble gliadin with AuNPs. The inventors found that 30 minutes resulted in poor adsorption of gliadin on the surface of the 20 nm AuNPs. Poor adsorption was characterised by poor pellet formation after centrifugation. Incubation at 90 minutes resulted in AuNP aggregation observed as a colour change from red to purple in some tubes. The inventors determined that 60 minutes of incubation was the preferred incubation period under these experimental conditions.

Solvent for Re-Dispersal of Gliadin-AuNP Pellet

The inventors investigated the effect of re-dispersing the gliadin-AuNP pellet in MilliQ water (FIG. 4), HEPES buffer (FIG. 5) and PBS buffer (FIG. 6) using dynamic light scattering. In each experiment, three different samples were measured: Sample 1 (red), Sample 2 (green) and Sample 3 (blue).

Shifting of peaks to the right indicates particles with an increased diameter correlating to an increase in the size of the particles, resulting from aggregation of the nanoparticles in the solution.

Figure 4:
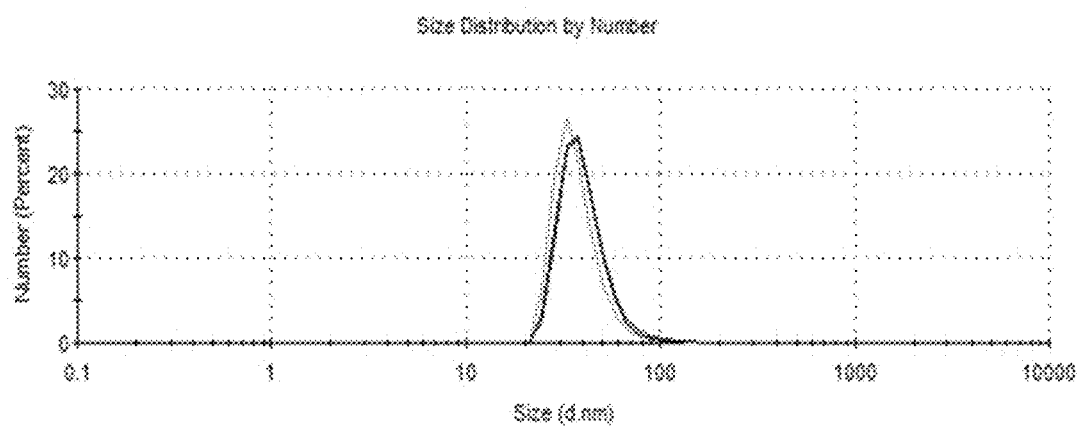
FIG. 4 shows the particle size distribution of 20 nm AuNPs adsorbed with gliadin when the pellet is re-dispersed in MilliQ water. No shift of peaks was determined for three different samples, indicating no increased aggregation.

As shown in FIG. 4, it was found that the peaks of gliadin-AuNPs re-dispersed with MilliQ water remained unchanged for three different samples. This indicated no relative change in the size of the particles and most importantly, indicated no aggregation amongst the gliadin-AuNPs.

Figure 5:
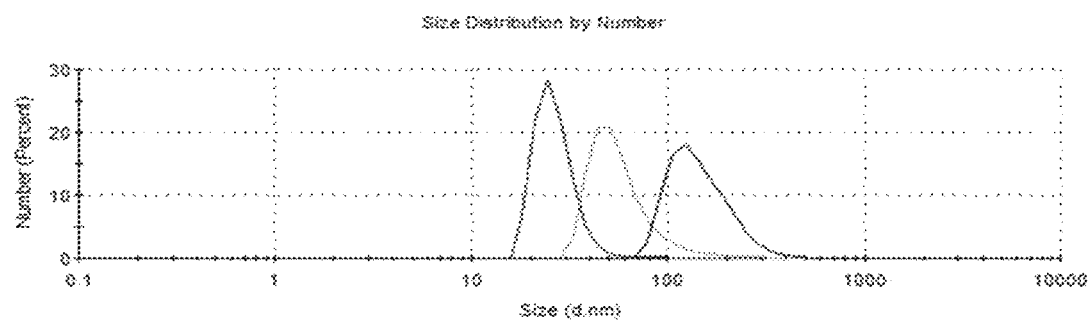
FIG. 5 shows the particle size distribution of 20 nm AuNPs adsorbed with gliadin when the pellet is re-dispersed in HEPES buffer. Measurements of three different samples show shifts of peaks to the right indicating increased aggregation.
Figure 6:
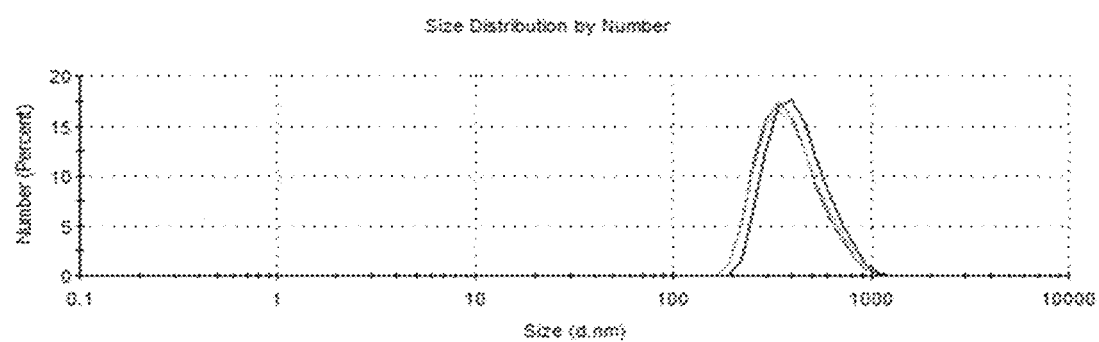
FIG. 6 shows the particle size distribution of 20 nm AuNPs adsorbed with gliadin when the pellet is re-dispersed in PBS buffer. Measurements of three different samples show shifts of peaks to the right aggregation.

As shown in FIG. 5, it was found that there was variation in the peaks observed for the three different samples. Peaks for Samples 2 and 3 showed shifts to the right indicating an increase in the size of gliadin-AuNPs, representing likely aggregation amongst the gliadin-AuNPs.

As shown in FIG. 6, it was found that again, the peaks showed a shift to the right, indicating an increase in the size of gliadin-AuNPs, representing likely aggregation amongst the gliadin-AuNPs.

From these results, the inventors determined that pellet re-dispersal in PBS buffer and HEPES buffer caused AuNP aggregation of the nanoparticles. This was be observed as a colour change from red to purple as well as an increased nanoparticle diameter in case of PBS and an increase in the diameter of the nanoparticles in the presence of HEPES buffer.

From these experiments, the inventors demonstrated that milliQ water was preferred as a solvent for re-dispersal of gliadin-AuNP pellet. Water is therefore preferred to re-disperse the gliadin-AuNP pellet formed in these methods. Purified water such as milliQ water is particularly preferred. Thus, purified water such as that defined by ISO 3696 is preferred for use in the present invention.

Ratio of AuNP to Gliadin

The inventors next sought to determine suitable ratios of AuNPs to gliadin to be used in the adsorption step. To do this, experiments were conducted using 20 nm AuNPs adsorbed with gliadin at different volume titrations for AuNPs and solubilised gliadin.

Figure 7:
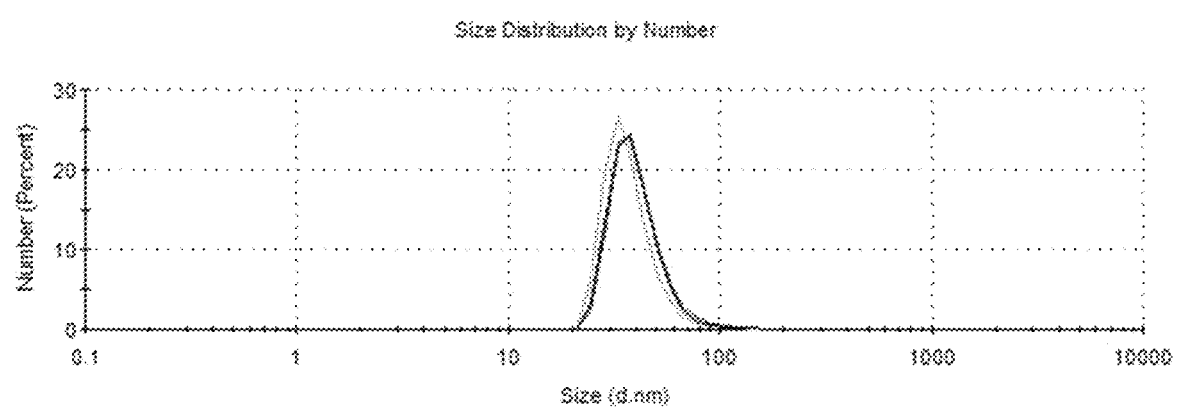
FIG. 7 shows the size distribution of 20 nm AuNPs adsorbed with gliadin when 600 μL of 20 nm AuNPs are added to 2800 μL of solubilised gliadin. Measurements of three different samples are plotted, which show stable sizes. No shifts of peaks the right indicate no aggregation.
Figure 8:
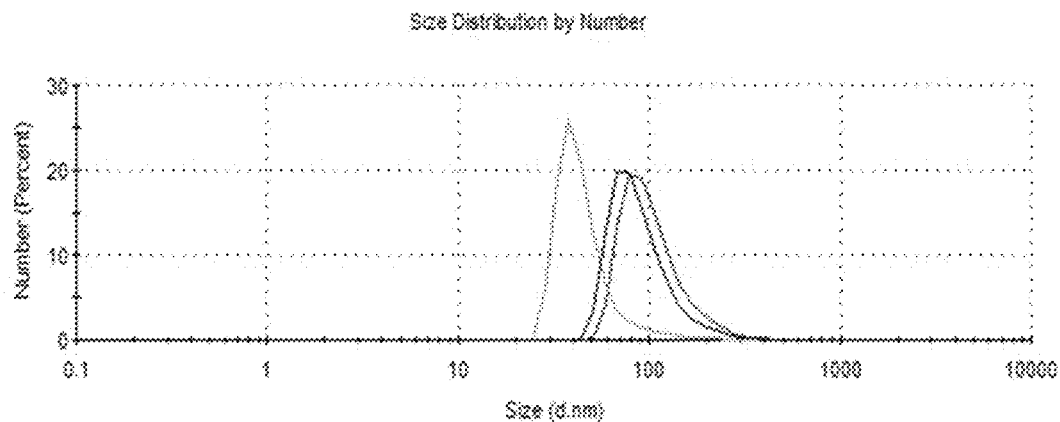
FIG. 8 shows the size distribution of 20 nm AuNPs adsorbed with gliadin when 600 μL of 20 nm AuNPs are added to 2000 μL of solubilised gliadin. Measurements of three different samples show shifts of peaks to the right indicating increased aggregation.
Figure 9:
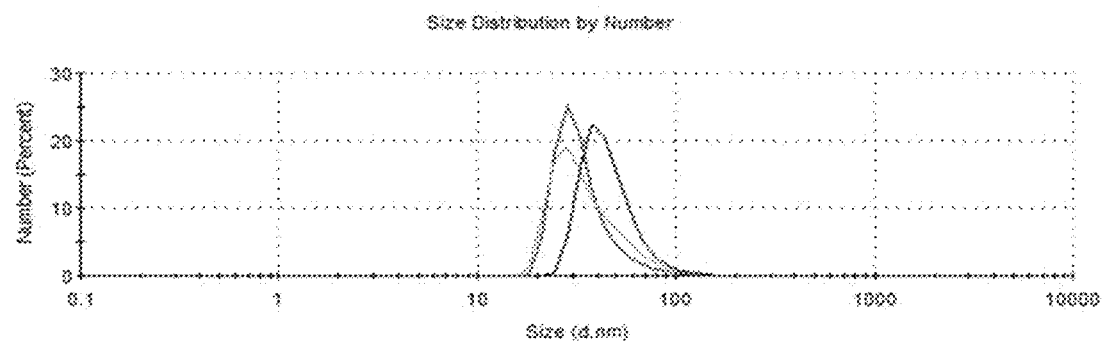
FIG. 9 shows the size distribution of 20 nm AuNPs adsorbed with gliadin when 300 μL of 20 nm AuNPs are added to 1000 μL of solubilised gliadin. Measurements of three different samples show shifts of peaks to the right indicating increased aggregation.
Figure 10:
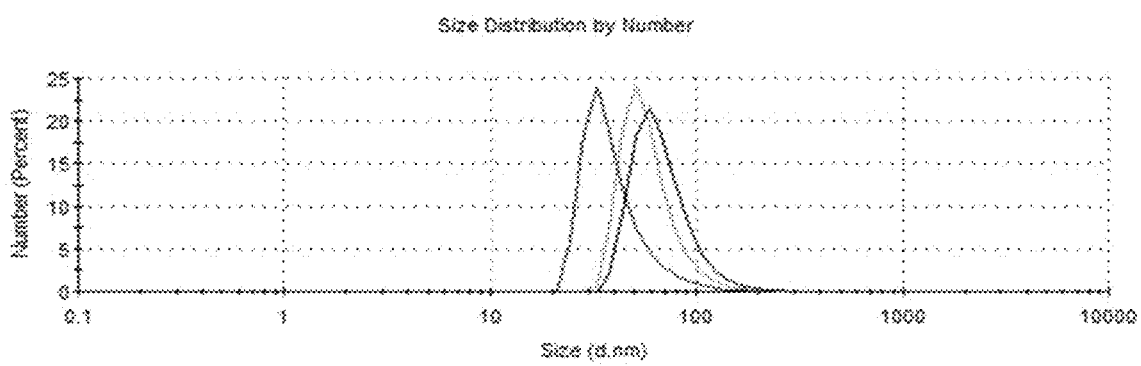
FIG. 10 shows the size distribution of 20 nm AuNPs adsorbed with gliadin when 100 μL of 20 nm AuNPs are added to 500 μL of solubilised gliadin. Measurements of three different samples show shifts of peaks to the right indicating increased aggregation.
Figure 11:
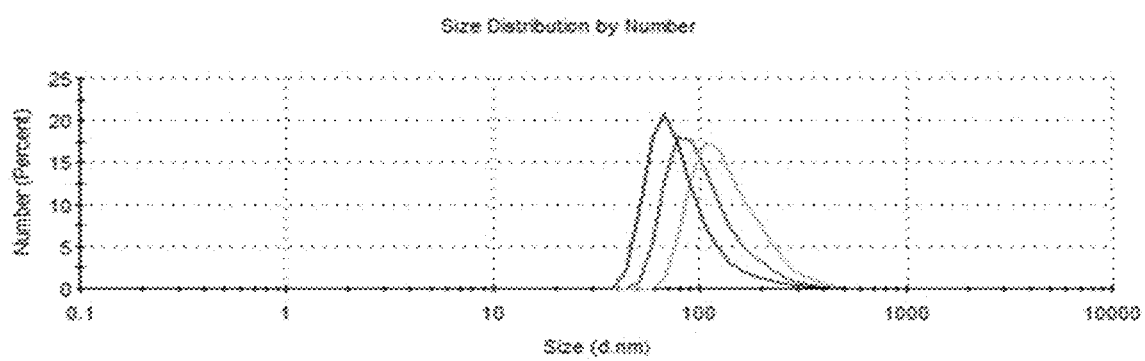
FIG. 11 shows the size distribution of 20 nm AuNPs adsorbed with gliadin when 150 μL of 20 nm AuNPs are added to 600 μL of solubilised gliadin. Measurements of three different samples show shifts of peaks to the right indicating increased aggregation.
Figure 12:
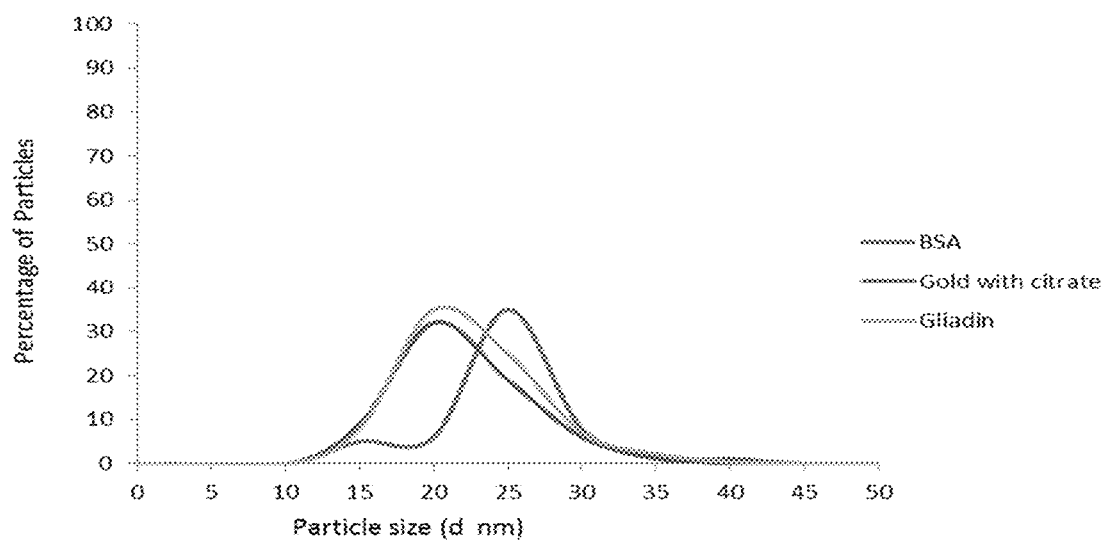
FIG. 12 shows results of dynamic light scattering for solutions containing AuNPs, gliadin-AuNP and BSA-AuNPs.

Experiments were Conducted in the Following AuNP:Gliadin Ratios:

600 µl:2800 µl (1:4.6) (FIG. 7)
600 µl:2000 µl (1:3.3) (FIG. 8)
300 µl:1000 µl (1:3.3) (FIG. 9)
100 µl:500 µl (1:5) (FIG. 10)
150 µl:600 µl (1:4) (FIG. 11)

As demonstrated in FIGS. 7-11, the inventors determined that a ratio of 20 nm AuNP to solubilised gliadin of 1:4.6 achieved a particularly beneficial extent of adsorption.

Example 5: Physical Characterisation of Gliadin Conjugation on AuNPs

The inventors next sought to determine if gliadin had indeed been conjugated to the gold nanoparticles (AuNPs), using dynamic light scattering (DLS).

Figure 13:
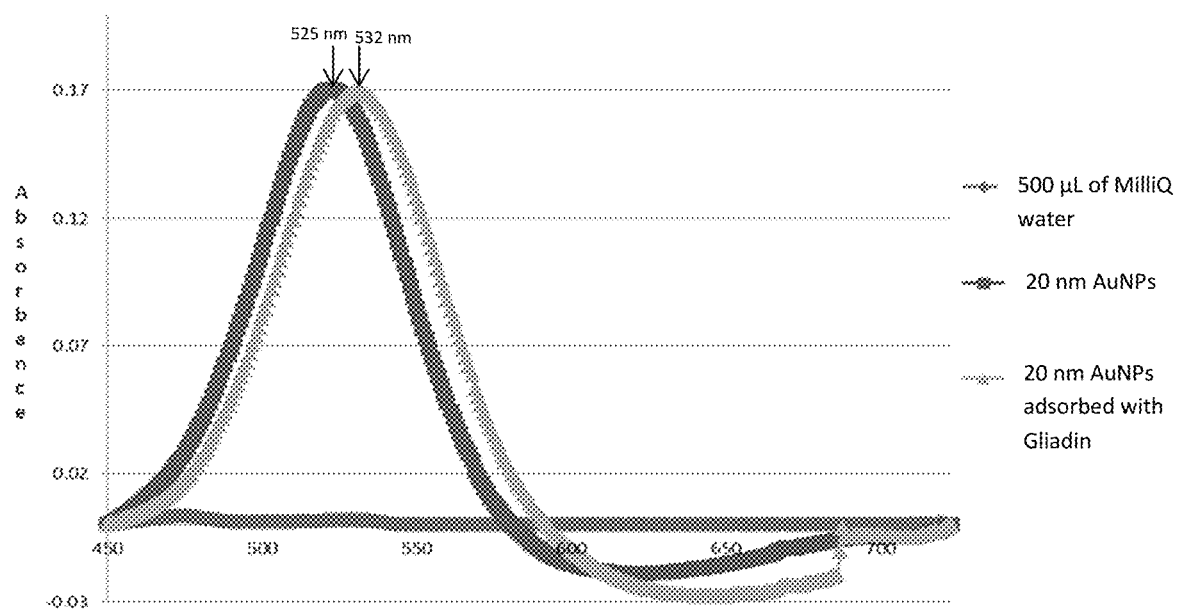
FIG. 13 shows results of UV-Vis absorption spectrophotometry for solutions containing gliadin-AuNP and 20 nm AuNP. When the same volume of 20 nm AuNP and 20 nm AuNP adsorbed with gliadin are compared, UV-Vis measurement indicates adsorption of gliadin with a spectral red shift in wavelength from 525 nm (for 20 nm AuNP only) to 532 nm (for 20 nm AuNP adsorbed with gliadin). This shift in wavelength confirms the adsorption of 20 nm AuNP with gliadin.
Figure 14:
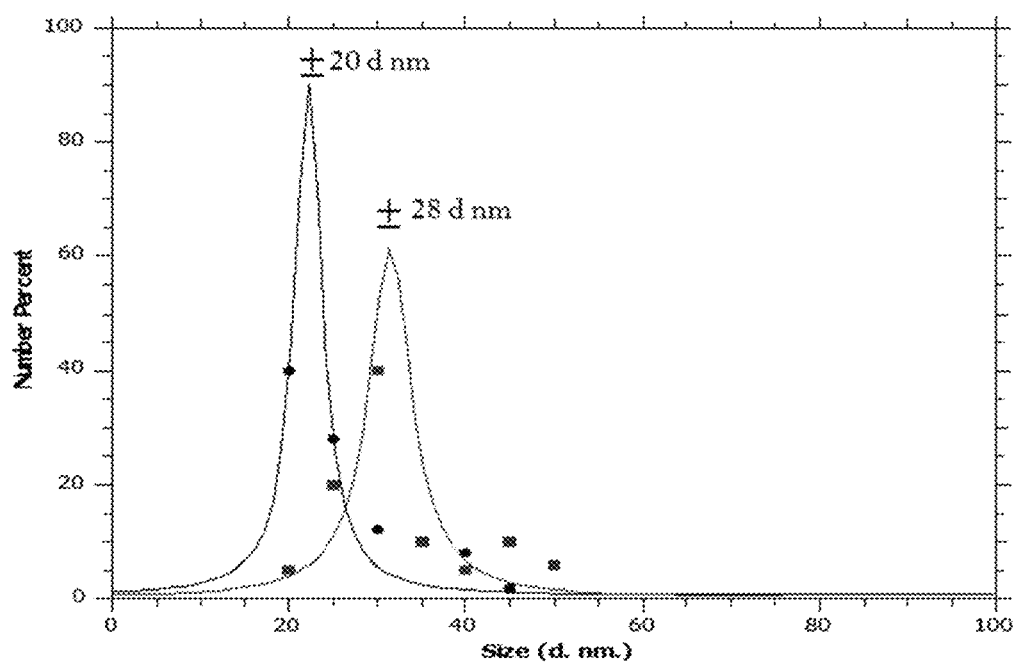
FIG. 14 shows an increase in size from 20 nm diameter to 28 nm diameter of the nanoparticles after adsorption with gliadin.

DLS measures the increase in particle hydrodynamic diameter as a consequence of ligand adsorption on the AuNP surface. DLS is a well-known analytical technique used for particle size analysis, and is particularly used for particle size determination in the nanometre range scale. As shown in FIG. 13, nanoparticles adsorbed with gliadin resulted in particles that were slightly larger in appearance compared with those that were not adsorbed with gliadin. From FIG. 14, DLS showed that the size of the gold colloids increased from 20 nm to 28 nm after adsorption of gliadin. No additional peaks were detected indicating the absence of aggregation in the solution.

As a control, nanoparticles conjugated with BSA also resulted in particles that were larger in appearance compared with those that were not adsorbed with BSA. As the molecular weight of a protein is directly proportional to its hydrodynamic radius (Dobrovolskaia et al. *Nanomedicine* 5(2): 106-117, 2009), the difference in the average diameter of gliadin-AuNPs and BSA-AuNPs was attributed to the molecular weight of each protein (BSA, MW 66.4 kDa; gliadin, MW 31 kDa).

Absorbance spectra were measured for 20 nm AuNP and 20 nm AuNP adsorbed with gliadin respectively between the wavelengths of 800 to 200 nm. UV-Vis measurements can be used to indicate adsorption of gliadin onto gold with a change in absorbance peak for the nanoparticle. For the 20 nm colloidal gold the typical absorbance maximum is at 525 nm. Upon adsorption of gliadin, the spectral analysis shows a shift in absorbance maximum from 525 nm to 532 nm (red-shift) indicating protein adsorption on the gold nanoparticle surface (FIG. 13).

Figure 15:
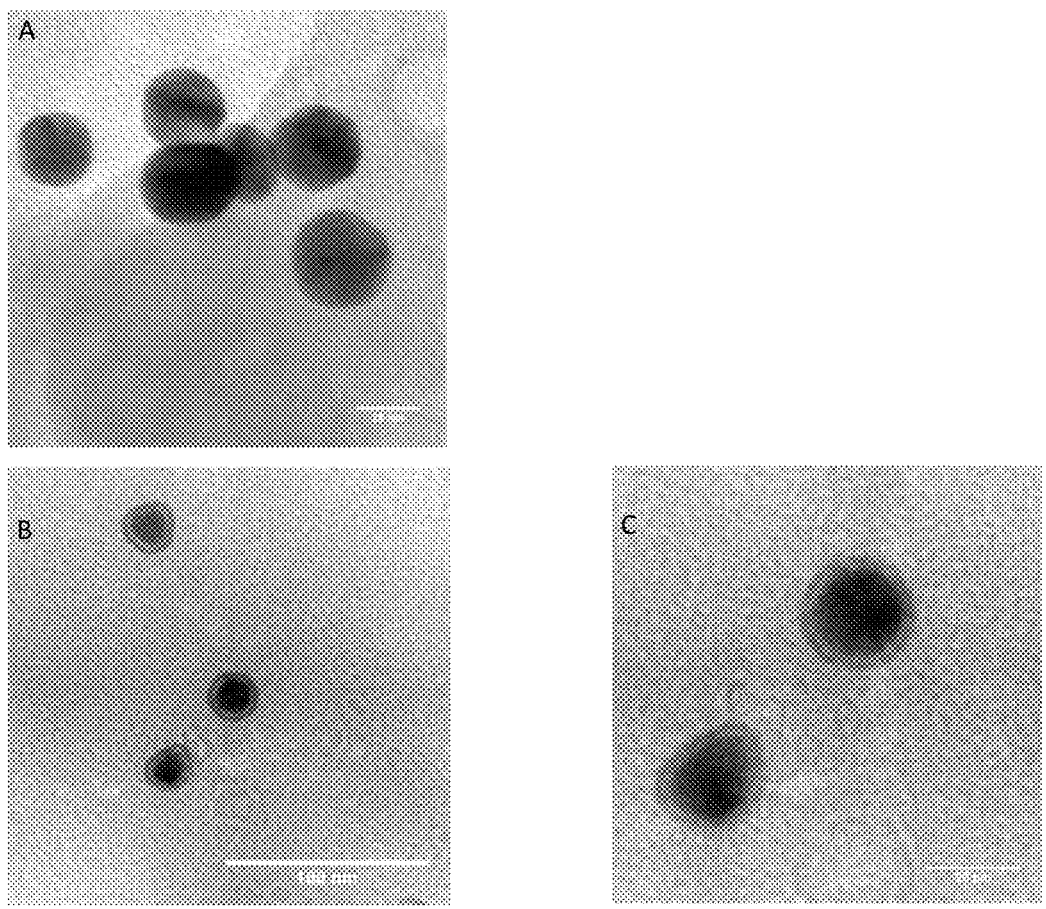
FIG. 15 shows high resolution Transmission Electron Microscopy (TEM) micrographs showing the adsorption of protein on the surface of 20 nm AuNP of (A) gold nanoparticle, (B & C) gold nanoparticle adsorbed with gliadin showing a white layer 'halo' surrounding the surface of the nanoparticles indicating coating of the gold with protein. The 'halo' effect is not present on the un-adsorbed gold nanoparticles. The halo indicates that multiple gliadin molecules are adsorbed on each nanoparticle.

TEM analysis of AuNPs revealed several aspects of their nature such as their shape, size and uniformity in preparation. 20 nm AuNPs show a relatively uniform spherical shape. On the other hand, high resolution imaging in 20 nm gold nanoparticles adsorbed with gliadin revealed a thin white layer of material (2-3 nm) surrounding the nanoparticles, which is not present prior to treatment (FIG. 15). This white layer is evidence of the adsorbed gliadin.

Example 6: Anti-Gliadin Antibody Binding to Gliadin-AuNPs

Figure 16:
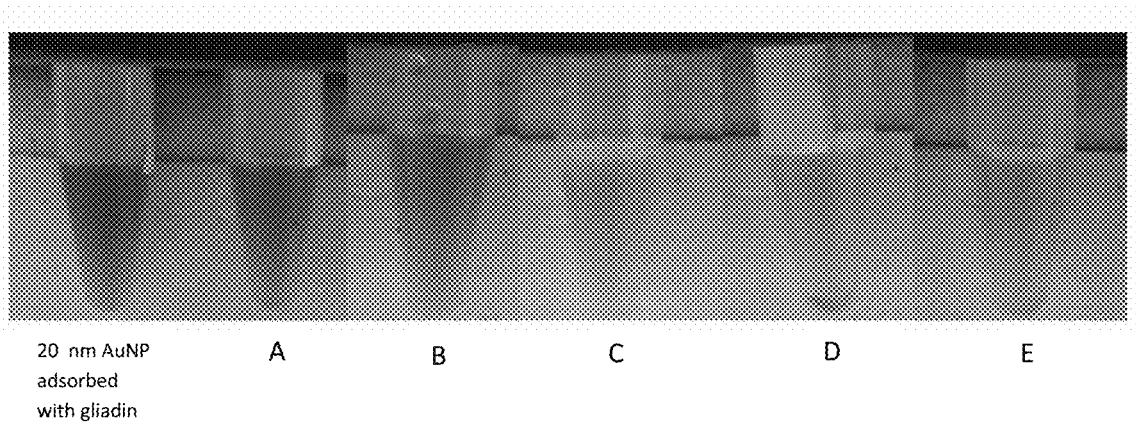
FIG. 16 shows the change in colour from red to transparent as observed in 20 nm AuNP adsorbed with gliadin in the presence of Anti-gliadin at different dilutions. Change in colour from red to transparent and precipitate formation was observed in 20 nm AuNP adsorbed with gliadin in the presence of anti-gliadin antibody at dilutions (A) 2 μg/mL, (B) 4 μg/mL, (C) 6 μg/mL, (D) 8 μg/mL and (E) 10 μg/mL and 20 nm AuNP adsorbed with gliadin alone.

The inventors sought to determine the capability of the gliadin adsorbed AuNPs to interact with anti-gliadin antibodies. The UV-Vis absorption spectra of solutions containing gliadin adsorbed gold nanoparticles and anti-gliadin antibody at increasing dilutions (2 µg/mL, 4 µg/mL, 6 µg/mL, 8 µg/mL and 10 µg/mL) were analysed using a Cary Series UV-Vis spectrophotometer (Agilent Technologies). The spectral analysis showed that when the anti-gliadin antibody up to a concentration of 10 m/mL was added to the 20 nm AuNPs adsorbed with gliadin, the absorbance peak decreased as compared to 20 nm AuNPs adsorbed with gliadin with no added antibodies. Therefore, the decrease in the absorbance peak suggests that the AuNPs coated with gliadin in the presence of the anti-gliadin antibody have increased nanoparticle to nanoparticle interactions. These inter-particle interactions lead to increased aggregation, which caused sedimentation that in turn led to a drop in absorbance. These spectral changes were also discernible by eye as a colour change from red to transparent (FIG. 16).

Figure 17:
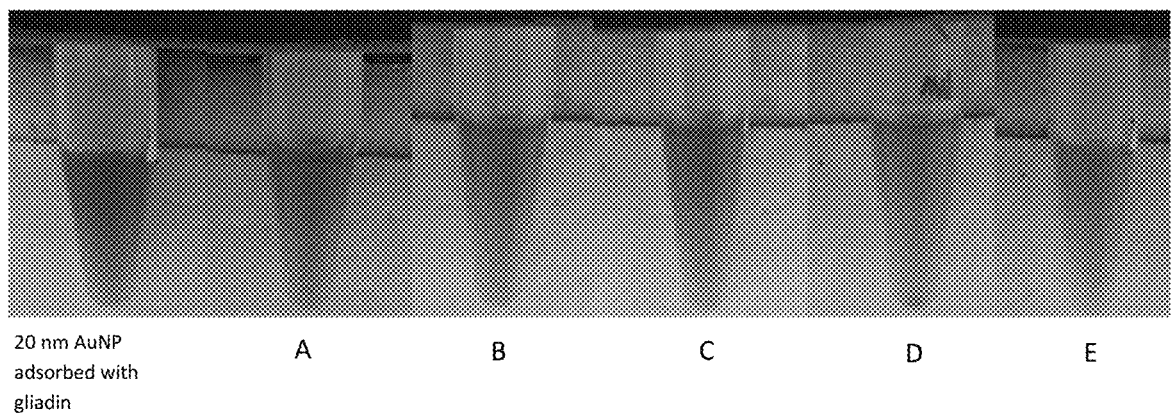
FIG. 17 shows no change in colour was observed in 20 nm AuNP adsorbed with gliadin in the presence of control antibody (IgG from rabbit serum) at different dilutions. No change in colour from red was observed in 20 nm AuNP adsorbed with gliadin in the presence of control antibody (IgG from rabbit serum) at dilutions (A) 2 μg/mL, (B) 4 μg/mL, (C) 6 μg/mL, (D) 8 μg/mL and (E) 10 μg/mL) and 20 nm AuNP adsorbed with gliadin alone.
Figure 18:
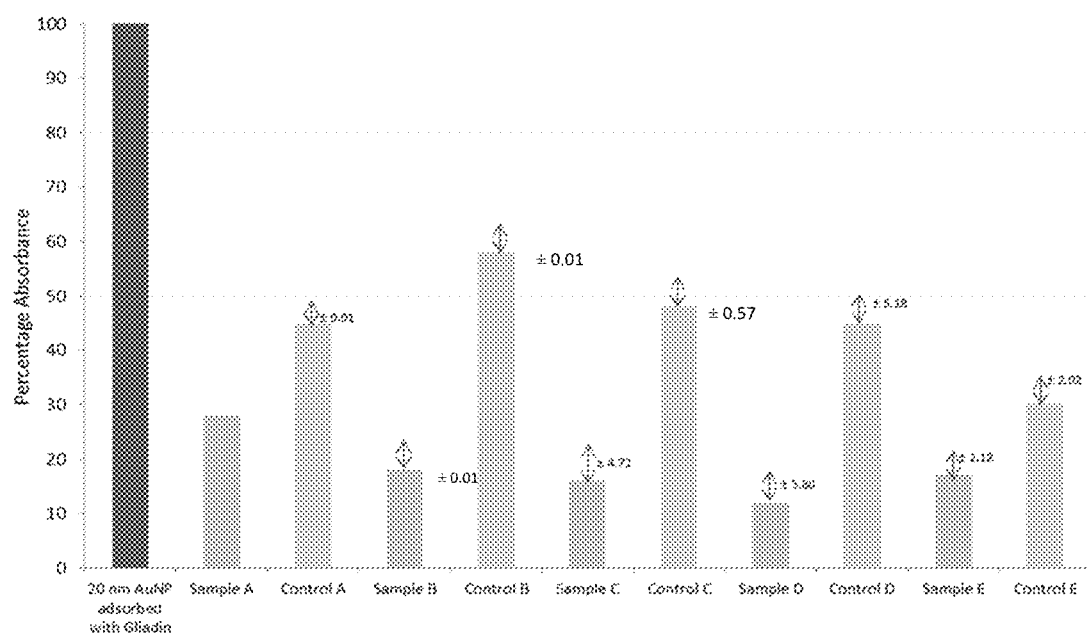
FIG. 18 shows the representation of specificity based on UV-Vis absorbance spectra for the antibody interactions at equal concentrations of anti-gliadin antibody and control antibody where (A) 2 μg/mL, (B) 4 μg/mL, (C) 6 μg/mL, (D) 8 μg/mL and (E) 10 μg/mL) and 20 nm AuNP adsorbed with gliadin alone.

In order to verify the specificity of the interaction between the gliadin adsorbed AuNPs and rabbit anti-gliadin antibody; another IgG antibody derived from rabbit, which antibody was not specific for gliadin (Sigma-Aldrich) was used as a control antibody. Following the addition of control IgG antibody, the 20 nm AuNPs adsorbed with gliadin showed a small decrease in absorbance but no change in colour or aggregation of nanoparticles was observed. Increasing volumes of MilliQ water were added to the samples in order to have constant final volume across all the antibody dilutions being tested. Therefore, the drop in absorbance values observed following addition of control antibody can be attributed to the dilution factor (FIGS. 17 and 18).

Figure 19:
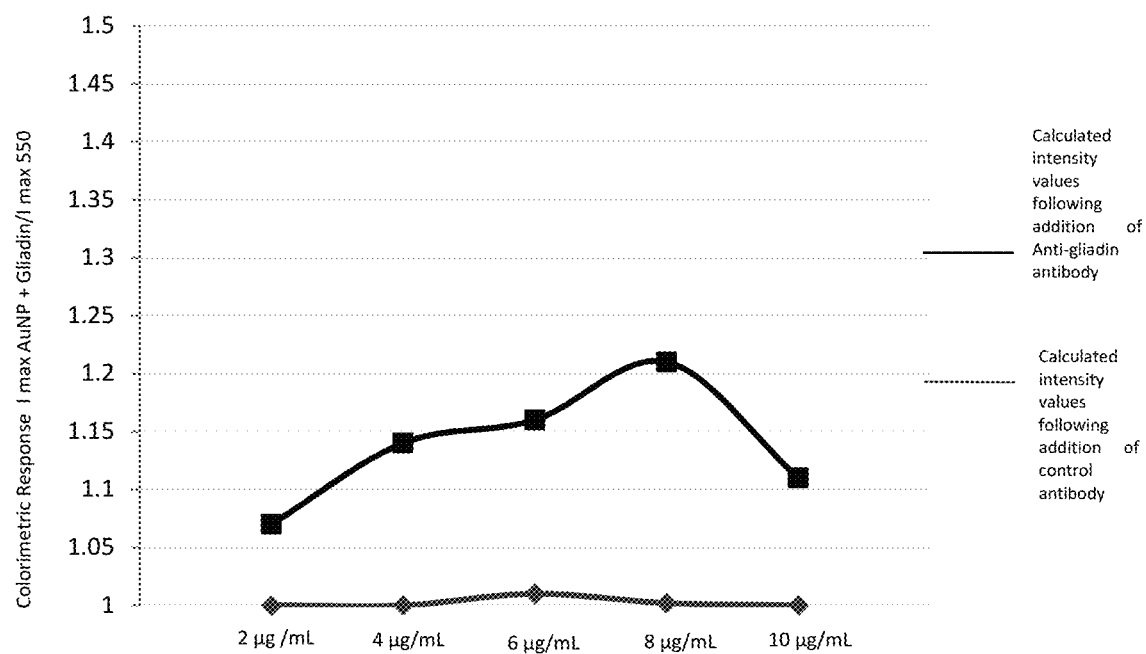
FIG. 19 shows the colorimetric response curve plotted in 20 nm AuNP adsorbed with gliadin in the presence of anti-gliadin antibody (top line) and the control antibody (IgG from rabbit serum; bottom line) at dilutions 2 μg/mL, 4 μg/mL, 6 μg/mL, 8 μg/mL and 10 μg/mL.

A colorimetric response curve, (which relates the concentration of the antibody to the 20 nm AuNPs adsorbed with gliadin) was plotted to represent the sensitivity values obtained for the different dilution values for both the anti-gliadin antibody and the control antibody (IgG from rabbit serum). A linear increase in the colorimetric response was observed, reaching a maximum value when anti-gliadin antibody is added at a concentration of 8 µg/mL to the 20 nm AuNP adsorbed with gliadin. The curve begins to drop when anti-gliadin antibody concentration is increased to 10 µg/mL. For the control antibody, the response curve behaves constant with only a slight increase at the control antibody dilution of 6 µg/mL. The near constant colorimetric response curve obtained for the control antibody as compared to the response curve obtained for anti-gliadin antibody determines the sensitivity values following the interactions between the gliadin adsorbed AuNPs and the anti-gliadin antibody (FIG. 19).

In a further control experiment, UV-Vis absorption spectra analysis showed that there was no change in the absorption wavelength of the BSA-AuNPs following the addition of the anti-gliadin antibody.

Example 7: Anti-Gliadin Antibody Binding to Gliadin-AuNPs in Saliva

Figure 20:
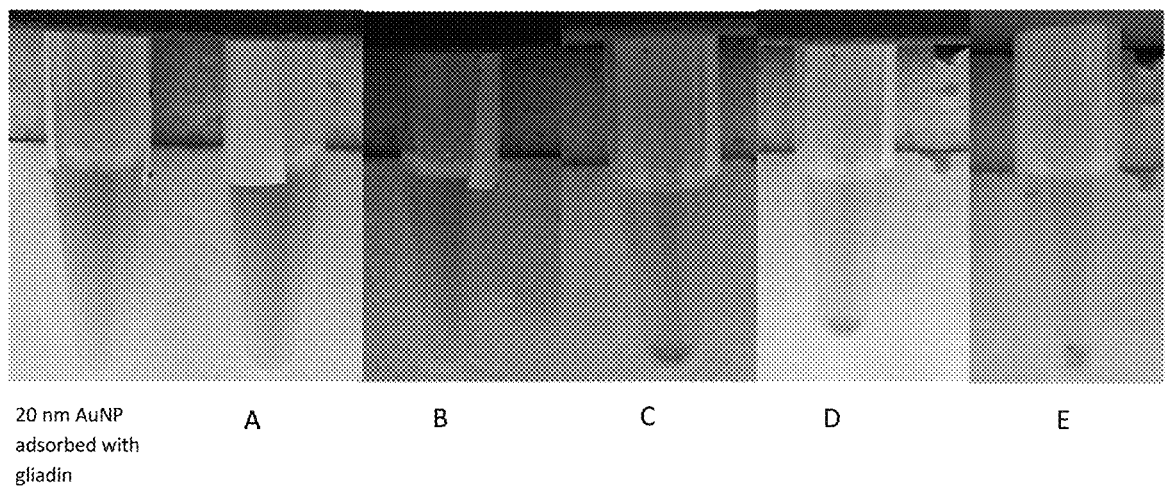
FIG. 20 shows the change in colour from red to transparent was observed in 20 nm AuNP adsorbed with gliadin in the presence of anti-gliadin antibody present in human saliva at dilutions (A) 2 μg/mL, (B) 4 μg/mL, (C) 6 μg/mL, (D) 8 μg/mL and (E) 10 μg/mL) and 20 nm AuNP adsorbed with gliadin alone.
Figure 21:
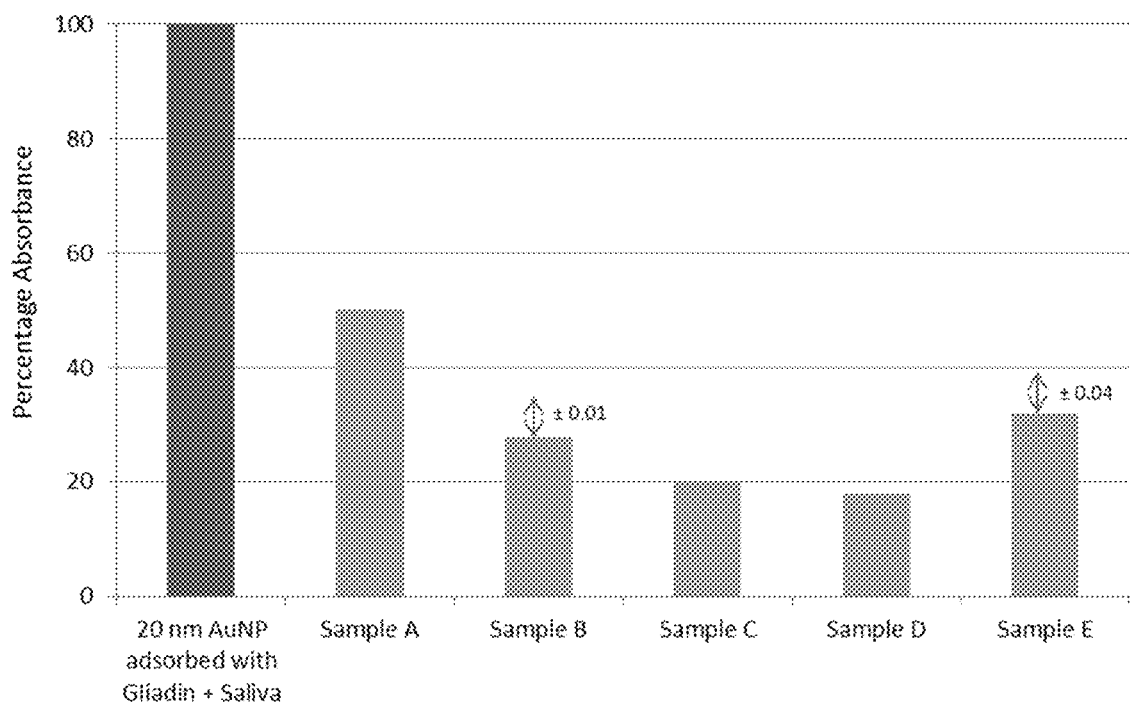
FIG. 21 shows the specificity of gliadin adsorbed nanoparticles in the presence of saliva containing anti-gliadin antibodies based on UV-Vis absorbance spectra. Antibody at dilutions (2 μg/mL, 4 μg/mL, 6 μg/mL, 8 μg/mL and 10 μg/mL) and the absorbance spectra of normal saliva added to 20 nm AuNP adsorbed with gliadin are plotted.

Using UV-Vis spectrophotometry, the inventors sought confirmation that the gliadin-AuNP were able to interact with anti-gliadin antibodies in saliva samples. A decrease in the absorption wavelength was observed when the gliadin adsorbed AuNPs were added to saliva samples containing anti-gliadin antibodies. Normal saliva itself did not show any absorbance and behaved like water with zero absorbance value. These readings confirmed that the anti-gliadin antibodies can cause aggregation in the presence of saliva and their specificity is not affected by other constituents in saliva. A change in colour from red to transparent was also observed (FIGS. 20 and 21).

Figure 22:
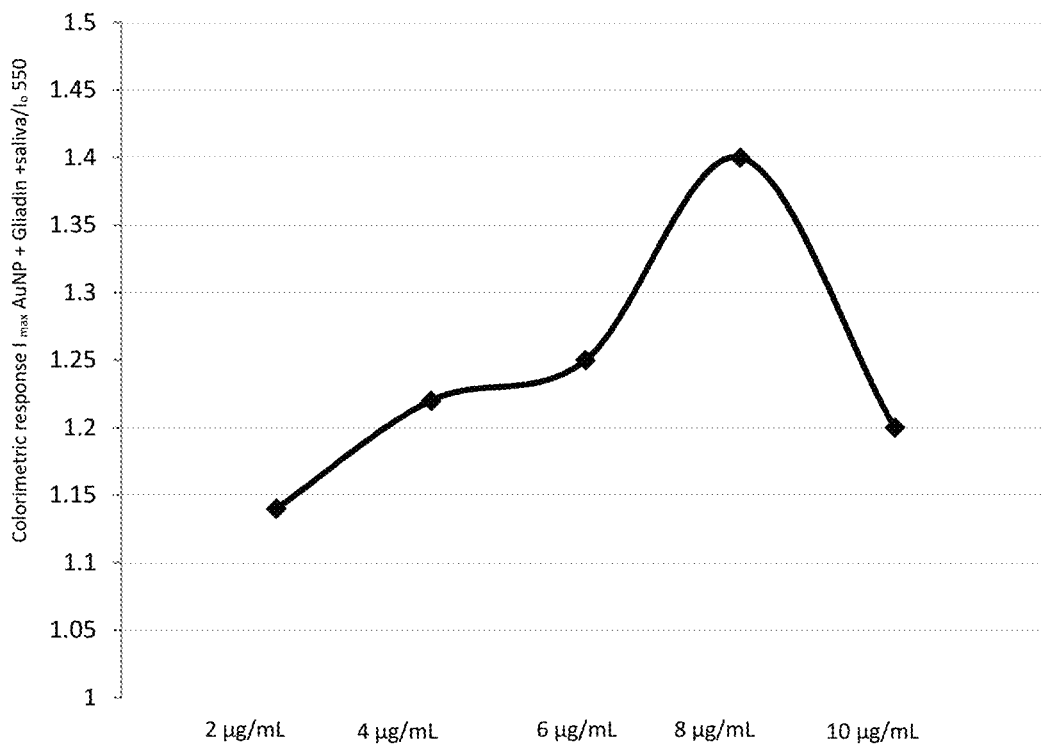
FIG. 22 shows the colorimetric response curve plotted for 20 nm AuNP adsorbed with gliadin in saliva following the addition of Anti-gliadin antibody at dilutions 2 µg/mL, 4 µg/mL, 6 µg/mL, 8 µg/mL and 10 µg/mL.

A colorimetric response curve was plotted to represent the sensitivity values obtained for the different dilution values. A linear increase in the colorimetric response was observed, reaching a maximum value when anti-gliadin antibody is added at a concentration of 8 µg/mL to 20 nm AuNPs adsorbed with gliadin in the presence of saliva. The response curve begins to show a drop in the colorimetric response value when the anti-gliadin concentration is increased to 10 µg/mL (FIG. 22). These antibody concentrations are similar to those normally occurring in coeliac patients' saliva (Lenander-Lumikari et al. *Archives of Oral Biology* 45(5): 347-54 2000 and Tucker et al. *J Pediatr* 113:286-289, 1988).

Example 8: Anti-Gliadin Antibody in Human Serum Binding to Gliadin-AuNPs

After demonstrating that the gliadin-AuNPs were able to interact with anti-gliadin antibodies in saliva samples, the inventors sought to demonstrate that gliadin-AuNPs are also able to interact with anti-gliadin antibodies in human serum samples.

Figure 23:
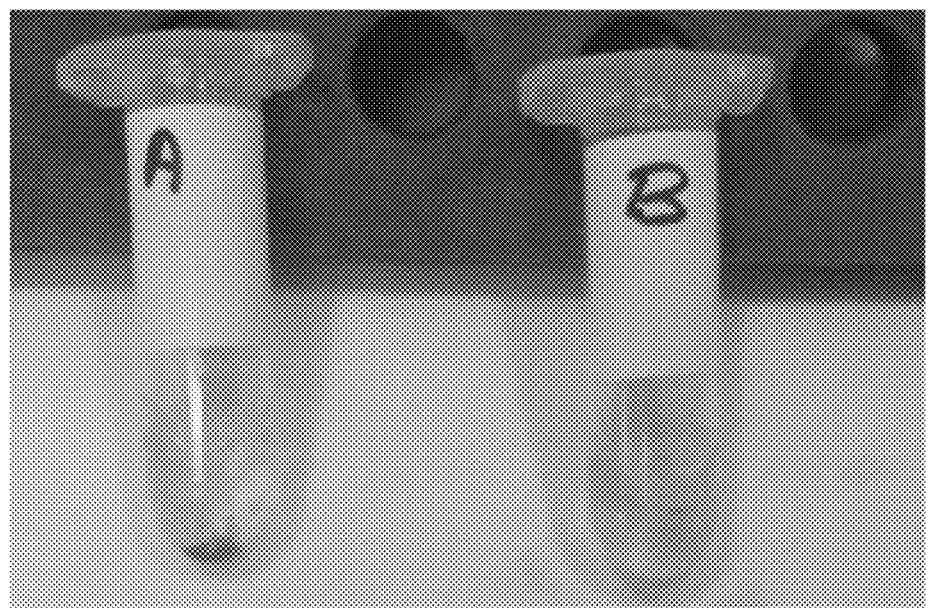
FIG. 23 shows the difference observed between tube A and control tube B. Tube A contains 20 nm AuNPs adsorbed with gliadin in the presence of anti-gliadin antibody added to human serum diluted to 1:50. Tube A shows a change in colour from red to transparent as well as a precipitate formation. Precipitate formation indicates aggregation of the nanoparticle adsorbed with a gliadin molecule which also indicates that an individual has gluten-related disorder. In control tube B, no anti-gliadin antibody is added. Control tube B shows no change in colour and remained red as well as the absence of any precipitate formation.

The experiments were performed as described in Example 1 above. The inventors observed that in tube A (FIG. 23), which contained 20 nm AuNPs adsorbed with gliadin in the presence of anti-gliadin antibody added to human serum diluted to 1:50, there is an increase in aggregation of the nanoparticles which causes the formation of a precipitate. Precipitate formation was detectable by eye. Precipitate formation indicates aggregation of the nanoparticles adsorbed with gliadin, indicating the presence of anti-gliadin antibodies in the sample (which also indicates that an individual has gluten-related disorder). The inventors also noted a change in the colour of the solution discernible by eye, from red to transparent.

In control tube B (FIG. 23) where no anti-gliadin antibody was added, the inventors observed that in the absence of anti-gliadin antibodies, there was no precipitate formation. This means that the nanoparticles did not aggregate and remained as a colloidal suspension after 30 minutes of incubation at room temperature. Additionally, the inventors did not observe any changes in colour of the solution which remained red.

Example 9: Analysis of the Interaction of Gliadin Au-NPs with Anti-Gliadin Antibodies in Human Serum Serum Assay Normal serum was diluted to 1:10, 1:20 and 1:50 using 10 mM HEPES buffer. 75 µL of serum from each of the dilutions was spiked with anti-gliadin antibody at various dilutions comparable to that seen in coeliac patients. To prevent non-specific binding, 1 µl of 20% BSA dissolved in MilliQ water was used as the blocking agent and was added to 20 nm AuNPs adsorbed with gliadin. The tubes were incubated for 30 minutes at room temperature. 75 µL of normal serum spiked with anti-gliadin antibody at increasing dilutions of 2 µg/mL, 4 µg/mL, 6 µg/mL, 8 µg/mL and 10 µg/mL was then added to 20 nm AuNPs adsorbed with gliadin in a biosafety cabinet. The tubes were then incubated for 30 minutes at room temperature.

Evaluation of the Clinical Human Serum Pool

Individual sera were obtained from the Walter and Eliza Hall Institute of Medical Research (WEHI), Melbourne. The clinical samples consisted of 30 human serum samples that were analysed in a randomised blind study. No prior knowledge on the coeliac disease status or any other clinical condition for any of the patient samples was known while testing.

Prior to testing, each human serum sample was diluted to 1:10, 1:20 and 1:50 using 10 mM HEPES buffer. 1 µl of 20% BSA dissolved in MilliQ water was added to 20 nm AuNPs adsorbed with gliadin to prevent non-specific binding. 75 µL of serum from each of the dilutions was then added to 20 nm AuNPs adsorbed with gliadin. The tubes were incubated for 15 minutes at room temperature before the absorbance was measured using a UV-Vis spectrophotometer.

Concentration and Purification of Immunoglobulins in Human Serum

Whole serum clinical samples obtained for the validation study were thawed at room temperature and 200 µL of each serum sample was pipetted in to a low-protein binding 1.5 mL Eppendorf tube and centrifuged at 6000 rpm for 15 minutes. The supernatant was removed, and the serum samples were diluted by adding 200 µL of 10 mM PBS. An equal volume of saturated ammonium sulphate solution was added slowly to achieve a 33% saturated (v/v) final concentration with continuous stirring of the tubes. The tubes were kept at 4° C. for 30 minutes and then centrifuged again at 5000 rpm for 15 minutes. The supernatant was removed, and the pellet was re-suspended by adding 200 µL of 10 mM PBS. The concentrated serum solution was stored at 20° C. until further use.

Zeba™ Spin desalting columns (Thermo Scientific™) were used for the de-salting of the immunoglobulins from the concentrated serum solution according to the manufacturer's instructions. Briefly, each column was prepared by centrifuging the column at 2000 rpm for 1 minute to remove the storage solution. The column was then washed three times with 300 µL of 10 mM HEPES Buffer which was used as the equilibration buffer for column preparation. 100 tit of the concentrated immunoglobulins from whole human serum were then passed through the column by centrifuging at 2000 rpm for 2 minutes. The flow-through was collected, the final concentration of the total immunoglobulins was measured using the NanoDrop and stored at −20° C. until further use.

Colorimetric Response Curve

A colorimetric response curve was plotted to represent the sensitivity values obtained for the different dilution values for both the anti-gliadin antibody and the control antibody (IgG from rabbit serum). The assay sensitivity was determined based on the colorimetric response values calculated as Colorimetric Response=I max at 532 nm/I at 550 nm i.e. spectral absorbance value obtained at 532 nm which is the wavelength where AuNP adsorbed with gliadin shows maximum absorbance by itself (no antibodies are added) divided by the absorbance at 550 nm where a shift in absorbance is observed following the interaction of the antibody to the AuNP adsorbed with gliadin.

As saliva and serum are complex fluids containing several proteins and factors that can affect the interaction of the AuNP adsorbed with gliadin with the antibodies, the assay sensitivity in spiked saliva and serum was calculated as Colorimetric Response=I max at 580 nm/I at 532 nm i.e. absorbance value obtained at 580 nm, which is the wavelength where a shift in absorbance is observed following the interaction of the antibody to the AuNP adsorbed with gliadin in saliva/serum divided by the maximum absorbance value of AuNP adsorbed with gliadin in saliva/serum.

Assay Development for Testing Antibodies in Serum

Figure 24:
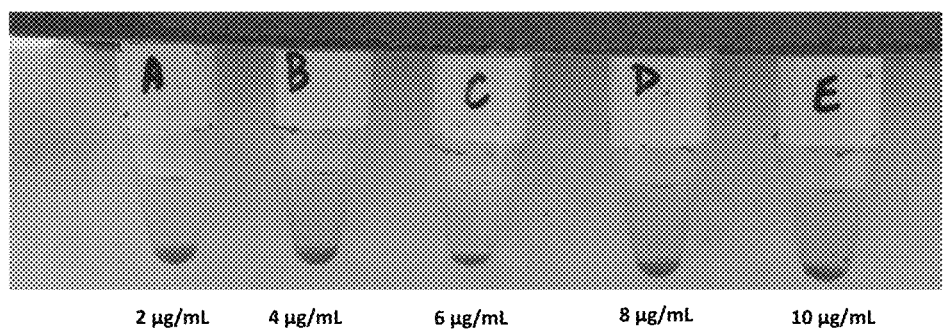
FIG. 24 shows that the specificity of the assay is not affected by other constituents in human serum. Different concentrations of anti-gliadin antibody (2 µg/mL, 4 µg/mL, 6 µg/mL, 8 µg/mL and 10 µg/mL) were added to titrated human sera and 20 nM of AuNP adsorbed with gliadin. A change in colour from red to transparent was observed for all anti-gliadin antibody concentrations.

Human serum was titrated, and anti-gliadin antibody was added at different concentrations to the diluted human serum. It was observed that following the addition of increasing concentrations of the anti-gliadin antibody, there was an increase in aggregation of the nanoparticles which causes the formation of a precipitate. This precipitate formation was detectable by eye and it indicates aggregation of the nanoparticles adsorbed with gliadin. A change in the colour of the solution that was discernible by eye, from red to translucent was also observed (FIG. 24).

Figure 25:
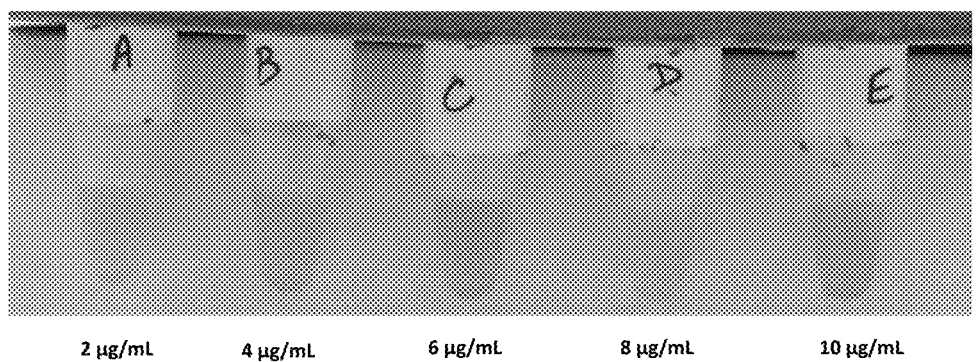
FIG. 25 shows that in the absence of anti-gliadin antibody, there is no colour change when human serum is incubated with AuNP adsorbed with gliadin. In this experiment, different concentrations of IgG antibody (2 µg/mL, 4 µg/mL, 6 µg/mL, 8 µg/mL and 10 µg/mL) were added to titrated human sera and 20 nM of AuNP adsorbed with gliadin.

The UV-vis absorbance spectra showed a decrease in absorbance when anti-gliadin rabbit antibody was added to the human serum as compared to normal rabbit IgG added to human serum where no precipitate formation was observed. Additionally, no change in colour was observed (FIG. 25). Normal serum itself did not show any absorbance and behaved like water with zero absorbance value. These readings confirmed that the anti-gliadin antibodies can cause aggregation in the presence of serum and their specificity is not affected by other constituents in serum.

Determination of Sensitivity Analysis in Serum

Figure 26:
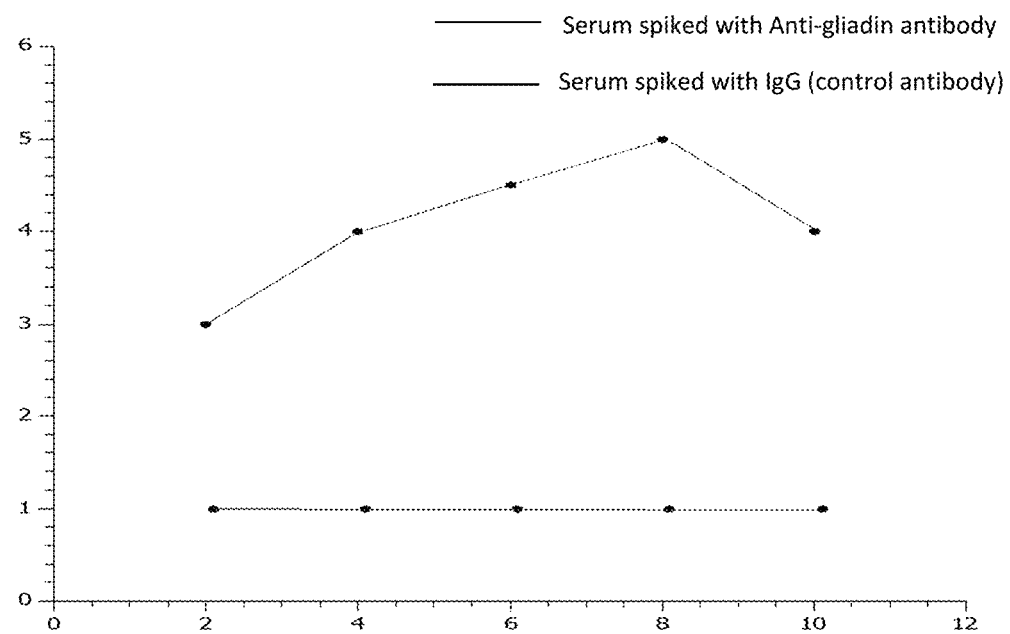
FIG. 26 shows the colorimetric response curve plotted in AuNP adsorbed with gliadin in 1:20 diluted serum following the addition of anti-gliadin antibody (top line) at dilutions 2 µg/mL, 4 µg/mL, 6 µg/mL, 8 µg/mL and 10 µg/mL compared to diluted serum spiked with IgG antibody (bottom line) at the same dilutions.

As can be seen in FIG. 26, an increase in the colorimetric response was observed, reaching a maximum value when 8 µg/mL of anti-gliadin antibody is added to the AuNPs coated with gliadin. The curve begins to drop at 10 µg/mL of anti-gliadin antibody. For the control antibody, the response curve behaves constant at all concentrations. These results are very similar to those observed above using either rabbit antibody in buffer or human saliva where in all cases the peak sensitivity was found at the level of 8 µg/mL anti gliadin IgG.

Example 10: Assay Validation by Testing Clinical Samples

Serum samples obtained from patients affected from coeliac disease (CD) were tested using the assay developed based on the AuNPs adsorbed with gliadin. Prior to testing, each human serum sample was diluted 1:20 using 10 mM HEPES buffer. The total immunoglobulins in human serum were concentrated using the ammonium sulphate method, purified using Zebra™ Spin desalting columns (Thermo Scientific™) and then allowed to react with AuNPs adsorbed with gliadin.

Based on the interaction of the antibody with the antigen, the samples were divided into three categories: precipitation, suspension and solution. It was found that out of the thirty clinical samples tested, twenty samples began to start forming a pellet within 15 minutes of incubation and were deemed positive for CD. Seven samples begin to start showing the formation of suspended particles within 15 minutes, these samples were further observed and after 30 minutes, four samples showed pellet formation and were recorded as positive. For three samples, no precipitation or formation of suspended particles was observed within 15 minutes, and were determined to be negative for CD.

The assay sensitivity was determined based on the colorimetric response obtained for each serum sample and is calculated as Colorimetric Response=I max at 580 nm/I at 532 nm. Using this method, the calculated colorimetric response for normal serum i.e. serum without anti-gliadin antibody is 1 and this acts as the cut-off value. Therefore, for the clinical samples, based on the spectral absorbance data, a value of 1 or less than 1 is indicated as negative for coeliac disease and a value above 1 is indicated as coeliac disease positive. The results of the analysis using AuNP-anti-gliadin interaction in serum showed high sensitivity and specificity and are described in the Table 4 below along with the results reported using the existing serology and histology, based on the detection of anti-transglutaminase antibodies (tTG-IgA) and anti-deamidated gliadin protein antibodies (DGP-IgG; DGP-IgA).

TABLE 4

Comparison of patient samples using the AuNP-IgG test with existing histology and serological* testing methods

| Volunteer | Histology | tTG-IgA | DGP-IgG | DGP-IgA | New AuNP-IgG based Test |
|---|---|---|---|---|---|
| n.1 | CD inconclusive | 5 (<20) | 17 (<20) | | CD |
| n.2 | CD | 1 (<4) | 3 (<20) | | CD |
| n.3 | Non-CD | 0.1 (0-6) | 0.2 (0-6) | | Non-CD |
| n.4 | CD | >100 (<4) | 33 (<20) | | CD |
| n.5 | CD/T1DM | 121 (<20) | | | CD |
| n.6 | CD | >100 (<4) | >100 (<20) | | CD |
| n.7 | CD | 217 (<5) | >150 (<20) | 132 (<20) | CD |
| n.8 | CD | 13 (0-6) | 23 (0-6) | | CD |
| n.9 | CD | >100 (<5) | >100 (<20) | | CD |
| n.10 | CD | 11 (0-6) | 1.4 (0-6) | | CD |
| n.11 | CD | 9 (<4) | 97 (<20) | | CD |
| n.12 | CD | 18.2 (0 < 20) | 3 (0.20) | | Non-CD |
| n.13 | CD | 16 (0-20) | 7 (<20) | 5 (<20) | CD |
| n.14 | Non-CD | 4 (0-20) | | | Non-CD |
| n.15 | CD | 47 (<5) | 86 (<5) | | CD |
| n.16 | CD | 74 (0-20) | | | CD |
| n.17 | CD | 145 (0-20) | | | CD |
| n.18 | Non-CD | <5 (<5) | 22 (<20) | | CD |
| n.19 | Non-CD | 12 (0-6) | 18 (0-6) | | CD |
| n.20 | Non-CD | 11 (0-6) | 13 (0-6) | | CD |
| n.21 | CD | 57 (<4) | 93 (<20) | | CD |
| n.22 | CD | 149 (<20) | 63 (<20) | 31 (<20) | CD |
| n.23 | Non-CD | <5 (<5) | <20 (<20) | | CD |
| n.24 | CD | >100 (<4) | >100 (<20) | | CD |
| n.25 | Non-CD | 3.8 (<6) | 37 (<6) | | CD |
| n.26 | Indeterminate | 28 (0-6) | 22 (0-6) | | CD |
| n.27 | Non-CD | <5 (<5) | <20 (<20) | | Non-CD |
| n.28 | CD | 180 (0-6) | 21 (0-6) | | CD |
| n.29 | Indeterminate | 4.8 (0-6) | 22 (0-6) | | CD |
| n.30 | CD | 20 (0-6) | 8.1 (0-6) | | CD |

*Serology results are indicated as IgA or IgG levels followed by reference ranges in brackets.

Analysis of Clinical Samples Using AuNP-Gliadin Based Test

Figure 27:
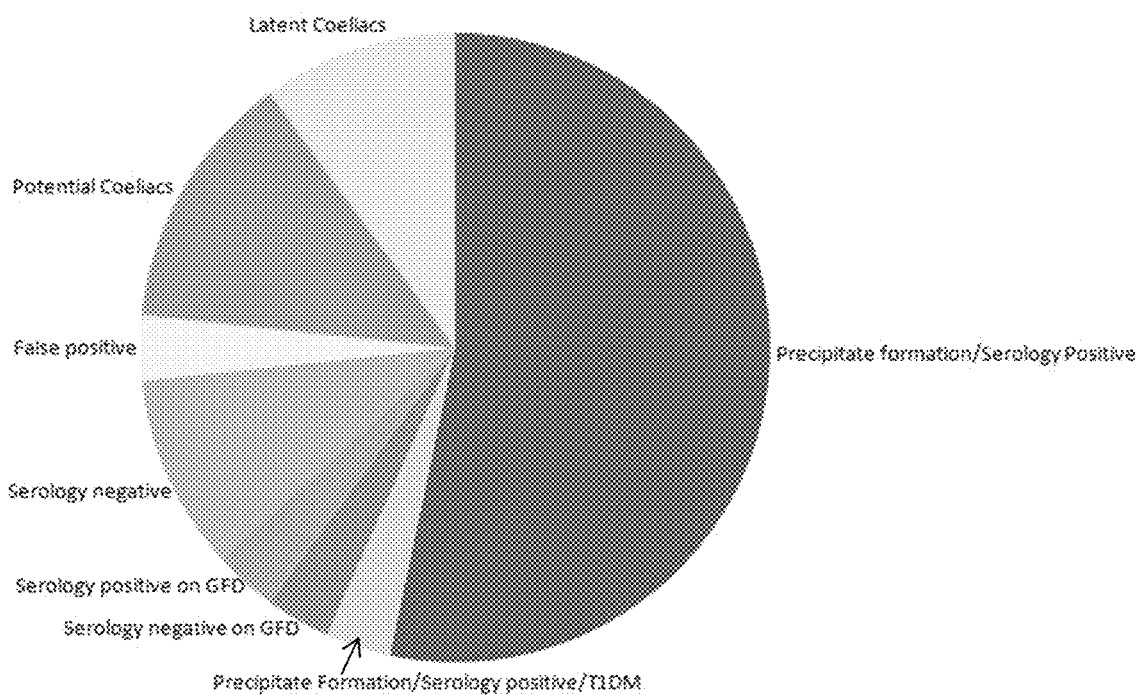
FIG. 27 is a schematic of the distribution of the results of the randomized and blinded clinical samples. Positive samples showed the formation of a precipitate and had a clear shift as well as drop in UV-Vis absorbance values as well as a high colorimetric response value.

The results of the randomized and blinded clinical samples tested in the inventors' assay were compared with the results reported using the existing serological and histology methods. These results for the 30 clinical samples are reported after the visual examination of precipitate formation and determination of shift or change in absorbance values using a UV-Vis spectrophotometer. The distribution of these samples is shown in FIG. 27.

Out of these thirty samples, sixteen samples that were diagnosed with active coeliac disease with high antibody titres as shown by serology and intestinal damage as per biopsy were identified as coeliac disease positive using the inventors' assay as well. These samples showed the formation of a precipitate and had a clear shift as well as drop in UV-Vis absorbance values as well as a high colorimetric response value.

In addition, there were three samples with inconclusive/indeterminate biopsy reports that had an unclear result and were tentatively placed under the broad sub-type of potential or latent coeliac. Using the inventors' diagnostic test, clear precipitate was obtained following the addition of the serum to the AuNP nanoparticles adsorbed with gliadin. The UV-Vis absorbance data supported the visual examination and these three samples were referred as positive for coeliac disease.

In addition, four clinical samples showed the formation of suspended nanoparticles along with a drop in UV-Vis absorbance values. These samples had negative biopsy reports but had positive or low positive serology results. The low-positive serology response of these samples could be the result of a low titre of tTG (tissue transglutaminase) or DGP (deamidated gliadin peptide) antibody in serum that affected the sensitivity of the existing assays. These four cases have been identified as potential coeliac disease sufferers by the inventors' diagnostic test method which has proven to be sensitive to detect low titres of anti-gliadin antibody in the sera.

In addition, the cohort consisted of two patients who had been previously diagnosed with coeliac disease and had later been placed on a gluten free diet (GFD). While one person had been following GFD for more than 2 months, the other person had been on a GFD for less than 2 weeks. In both these cases, while the biopsy results were positive for coeliac disease, the existing serological tests were negative in each of these cases. The inventors' diagnostic test, however, was more discriminatory and sensitive to the anti-gliadin antibody titres in serum and the inventors could clearly distinguish the person following a GFD for more than 2 months as negative for coeliac disease while the person who had been on a GFD for less than 2 weeks formed a suspension, indicating that the anti-gliadin titres might be very low but are still present in the serum. In both these cases, the positive result for the biopsy might be explained by the longer time taken to revert to normal intestine from a flat mucosa or subtotal villous atrophy. The correct and clear analysis of these two exceptional cases on a gluten free diet (GFD) for different time periods illustrates that this diagnostic test is sensitive to lowered anti-gliadin titres as well and can be used for monitoring patients on a GFD.

The cohort also contained a sample from one young child who was suffering from Type 1 diabetes mellitus (T1DM); the diabetic child could be identified as positive for CD using the existing methods. The prevalence of coeliac disease in T1DM is reported to vary from 3% to 16%, with a mean prevalence of 8% (Volta et al. *Expert Rev Gastroenterol Hepatol* 5:479-87, 2011). The higher risk for patients with T1DM to develop coeliac disease can be caused due to the common genetic background as well as the multiple environmental and immunological factors that increase the chance of developing coeliac disease (Ventura et al. Gut 51:897, 2002). Even though the prevalence rates for CD are higher in patients with T1DM, most patients' particularly diabetic children have silent form of the disease with the absence of both gastrointestinal and extra-intestinal signs or have subclinical forms of the disease such as anaemia or short stature and are often regarded as asymptomatic. As such, the early and correct diagnosis for such patients is difficult and such patients need to be kept on a gluten-containing diet with careful clinical and serological follow-up, as many develop villous atrophy on continued gluten exposure (Holmes et al. *Diabet Med* 18:169-77, 2001).

The inventors' diagnostic test could correctly identify this patient with T1DM as positive for coeliac disease and this matches with the previously conducted biopsy and serology profile of the patient. This result is of immense importance as it indicates sensitivity as well as the specificity of the AuNP-Gliadin nanoparticles to detect anti-gliadin antibodies in patients with unclear symptoms and suffering from other autoimmune diseases as well.

The cohort of clinical samples that was analysed in the inventors' validation study included four samples that were negative for coeliac disease based on biopsy and existing serological tests. While three samples were correctly identified as negative for coeliac disease by the inventors' diagnostic assay as well, one sample showed the formation of a suspension and was identified as positive. As intestinal biopsy has been used as the gold standard for CD confirmation, that one sample has been referred to as a false positive result. Overall, upon comparing the results for the 30 clinical samples, while 29 samples showed comparable results, 1 false positive result was obtained using the nanoparticle based diagnostic test method giving the inventors' test an overall sensitivity and specificity of 96.7%.

Example 11: Preparation, Characterisation and Clinical Sample Analysis of the Gold Nanoparticle Adsorbed with Peptide The inventors also sought to determine whether peptide (QLQPFPQPQLPYPQPQC; SEQ ID NO: 3) when adsorbed on the surface of the gold nanoparticles could be used to detect anti-gliadin antibody.

Peptide (QLQPFPQPQLPYPQPQC) was adsorbed on the surface of the gold nanoparticles in a 2-step protocol. In the first step, Avidin was adsorbed on the surface of the gold nanoparticles to obtain Avidin-AuNP particles followed by the binding of the peptide through a biotin-PEG-Maleimide linker molecule.

Adsorption of Avidin on the Surface of 20 nm AuNP 1 mg of Avidin in powdered form (Thermo-Fisher) was weighed and dissolved in 1 mL of MilliQ water to get a concentration of 1 µg/mL. 300 µL of 20 nm AuNP were added dropwise to 200 µL of dissolved Avidin in a 1.5 mL Eppendorf tube followed by a quick vortex. The tubes were incubated for 60 minutes at room temperature and were further stirred every 10 minutes. The solution was centrifuged at 4500 g for 30 minutes using Eppendorf® Microcentrifuge. The supernatant was discarded, and the pellet was re-dispersed in 200 µL of MilliQ water. The 20 nm AuNPs adsorbed with Avidin were stored at 4° C. until further use.

Binding of Peptide to Biotin-PEG-Maleimide 0.5 mg of peptide (QLQPFPQPQLPYPQPQC) was weighed and dissolved in 1 mL of MilliQ water in 1.5 mL Eppendorf tubes. The peptide was vortexed for a few minutes to enable complete solubilisation of the peptide.

Poly (ethylene glycol) [N-(2-maleimidoethyl)carbamoyl] methyl ether 2-(biotinylamino)ethane (i.e. Biotin-PEG-Maleimide) has a Mn 5,400 and a molecular weight of 345 Da with Maleimide at the $\Omega$-end and Biotin at the $\alpha$-end. 0.5 mg of Biotin-PEG-Maleimide was weighed and dissolved in 1 mL of MilliQ water in 1.5 mL Eppendorf tubes to obtain a final concentration of 0.5 µg/mL. 300 µL of the dissolved peptide is then added to 700 µL of Biotin-PEG-Maleimide linker molecule and left overnight at room temperature. Maleimide groups of the linker reacted efficiently and specifically with free (reduced) sulfhydryl's in the peptide sequence at pH 6.5-7.5 to form stable thio-ether bonds.

Binding of Peptide-Biotin-PEG-Maleimide to 20 nm AuNP Adsorbed with Avidin

The 20 nm AuNPs adsorbed with Avidin were centrifuged at 4500 g for 30 minutes using Eppendorf® Microcentrifuge. The supernatant was discarded, and the pellet was re-dispersed in 100 µL of Biotin-PEG-Maleimide to re-disperse the pellet. The tubes were kept at room temperature for 1 hour to allow the biotin end of the linker to interact with the Avidin protein adsorbed to the 20 nm AuNP such that one Avidin protein can bind up to four biotin molecules. The tubes were then centrifuged again at 4500 g for 5 minutes using an Eppendorf® Microcentrifuge. The supernatant was discarded, and the pellet was re-suspended in 100 µL of MilliQ water. The 20 nm AuNPs adsorbed with Avidin-Peptide-Biotin-PEG-Maleimide were stored at 4° C. until further use.

Physical Characterisation of Peptide Conjugation on AuNPs

To confirm that the peptide bound to Biotin-PEG-Maleimide had indeed been adsorbed to the gold nanoparticles (AuNPs) adsorbed with Avidin, the inventors again used Dynamic Light Scattering (DLS), Transmission Electron Microscopy (TEM) and UV-Vis Measurements as described in Example 1.

Immunoassay

The general immunoassay format used to assess the activity of AuNPs adsorbed with peptide with the antibodies is outlined below. Assay steps were performed at room temperature. Briefly, 150 µL of AuNPs adsorbed with peptide were added to 1.5 mL low protein binding Eppendorf® tubes. Anti-gliadin antibody from rabbit was added to each of the tubes in concentrations ranging from 2 µg/mL to 20 µg/mL to determine the specificity of the reaction between peptide adsorbed AuNPs and anti-gliadin antibody, IgG from normal rabbit serum was used as a control antibody and added to 150 µL of AuNPs coated with peptide in concentrations ranging from 2 µg/mL to 20 µg/mL MilliQ water was added to the tubes to bring the final volume in each Eppendorf tube up to 225 µL. The UV-vis absorption spectra of solutions containing peptide coated gold nanoparticles and anti-gliadin antibody at increasing dilutions (2 µg/mL, 4 µg/mL, 6 µg/mL, 8 µg/mL, 10 µg/mL, 12 µg/mL, 14 µg/mL, 16 µg/mL, 18 µg/mL and 20 µg/mL) were studied using a Cary Series UV-Vis spectrophotometer (Agilent Technologies). Readings were taken in duplicate and a student's t-test was used to determine the p value.

Concentration and Purification of Immunoglobulins in Human Serum

Whole serum clinical samples obtained for the validation study were thawed at room temperature and 200 µL of each serum sample was pipetted out to a low-protein binding 1.5 mL Eppendorf tube and centrifuged at 6000 rpm for 15 minutes. The supernatant was removed, and the serum samples were diluted by adding 200 µL of 10 mM PBS. An equal volume of saturated ammonium sulphate solution was added slowly to achieve a 33% saturated (v/v) final concentration with continuous stirring of the tubes. The tubes were kept at 4° C. for 30 minutes and then centrifuged again at 5000 rpm for 15 minutes. The supernatant was removed, and the pellet was re-suspended by adding 200 µL of 10 mM PBS. The concentrated serum solution was stored at 20° C. until further use.

Zeba™ Spin desalting columns (Thermo Scientific™) were used for the de salting of the immunoglobulins from the concentrated serum solution according to the manufacturer's instructions. Briefly, each column was prepared by centrifuging the column at 2000 rpm for 1 minute to remove the storage solution. The column was then washed three times with 300 µL of 10 mM HEPES Buffer which was used as the equilibration buffer for column preparation. 100 µL of the concentrated immunoglobulins from whole human serum were then passed through the column by centrifuging at 2000 rpm for 2 minutes. The flow-through was collected, the final concentration of the total immunoglobulins was measured using the NanoDrop and stored at −20° C. until further use.

Evaluation of the Clinical Human Serum Pool

Individual sera were obtained from the Walter and Eliza Hall Institute of Medical Research (WEHI), Melbourne. The clinical samples consisted of 30 human serum samples that were analysed in a randomised blind study. No prior knowledge on the coeliac disease status or any other clinical condition for any of the patient samples was known while testing.

Prior to testing, each human serum sample was diluted 1:20 using 10 mM HEPES buffer. The total immunoglobulins in human serum were concentrated using ammonium sulphate method and purified using Zeba™ Spin desalting columns (Thermo Scientific™). Following purification, the flow-through was collected and the final concentration of the total immunoglobulins was measured using the NanoDrop 1 µl of 20% BSA dissolved in MilliQ water was added to AuNPs adsorbed with peptide to prevent non-specific binding. 75 µL of concentrated and purified serum was then added to AuNPs adsorbed with peptide. The tubes were incubated for 45 minutes at room temperature before the absorbance was measured using a UV-Vis spectrophotometer.

Results

Characterisation of 20 nm AuNP Coated with Peptide

UV-Vis

Absorbance spectra were measured for 20 nm AuNP and 20 nm AuNP adsorbed with peptide respectively between the wavelengths of 800 to 200 nm. UV-vis measurements can be used to indicate adsorption of peptide onto gold with a change in absorbance peak for the nanoparticle or red-shift (Link S et al. *J. Phys. Chem. B*, 103:4212-4217, 1999). For the 20 nm, colloidal gold the typical absorbance maxima is at 525 nm. Upon adsorption of peptide, the spectral analysis shows a shift in absorbance maxima from 525 nm to 527 nm (red-shift) indicating peptide adsorption onto the gold nanoparticle surface (FIG. 28).

Figure 28:
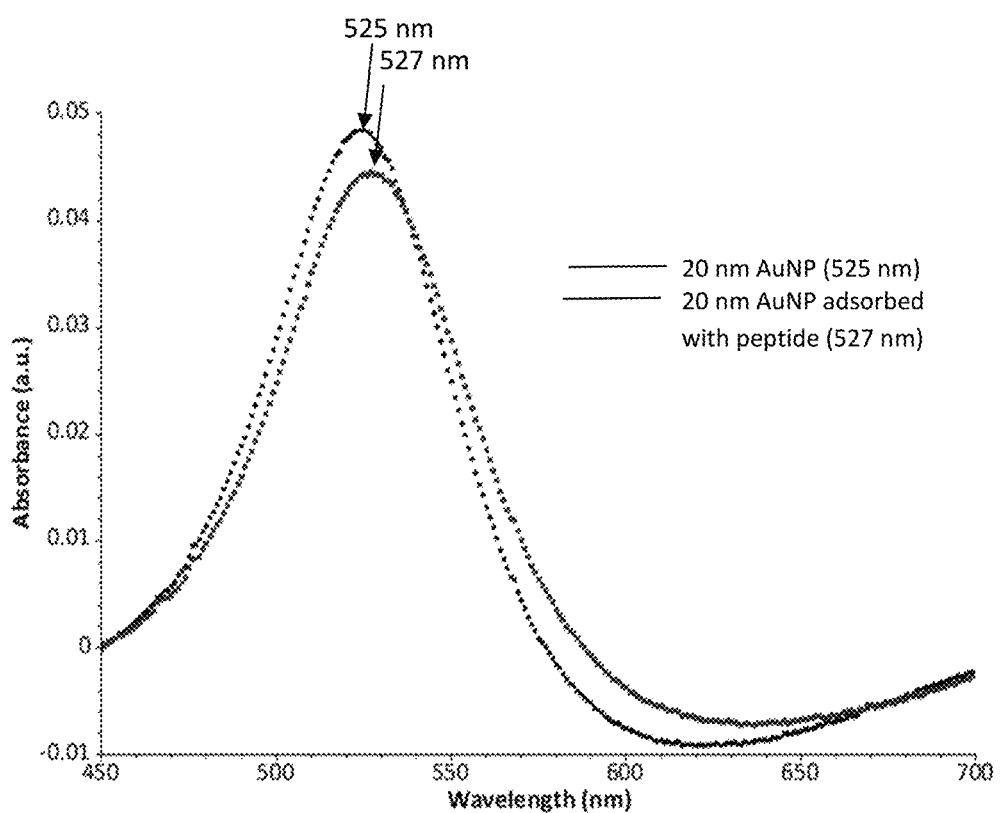
FIG. 28 shows results of UV-Vis absorption spectrophotometry for solutions containing AuNP and AuNP adsorbed with peptide QLQPFPQPQLPYPQPQC (SEQ ID NO:3). The peptide was adsorbed on the surface of the gold nanoparticles in a 2-step protocol. In the first step, Avidin was adsorbed on the surface of the gold nanoparticles to obtain Avidin-AuNP particles followed by the binding of the peptide through a biotin-PEG-Maleimide linker molecule. When the same volume of 20 nm AuNP and 20 nm AuNP adsorbed with peptide QLQPFPQPQLPYPQPQC are compared, the UV-Vis measurement indicates adsorption of peptide with a spectral red shift in wavelength from 525 nm (for 20 nm AuNP only) to 527 nm (for 20 nm AuNP adsorbed with peptide QLQPFPQPQLPYPQPQC). This shift in wavelength confirms the adsorption of AuNP with peptide QLQPFPQPQLPYPQPQC.

FIG. 28 represents the characterisation of AuNP adsorbed with peptide using a UV-Vis Spectrophotometer. When the same volume of 20 nm AuNP and 20 nm AuNP adsorbed with peptide are compared, the UV-Vis measurement indicates adsorption of peptide with a spectral red shift in wavelength from 525 nm (for 20 nm AuNP only) to 527 nm (for 20 nm AuNP adsorbed with peptide). This shift in wavelength confirmed the adsorption of AuNP with peptide.

Dynamic Light Scattering (DLS)

Figure 29:
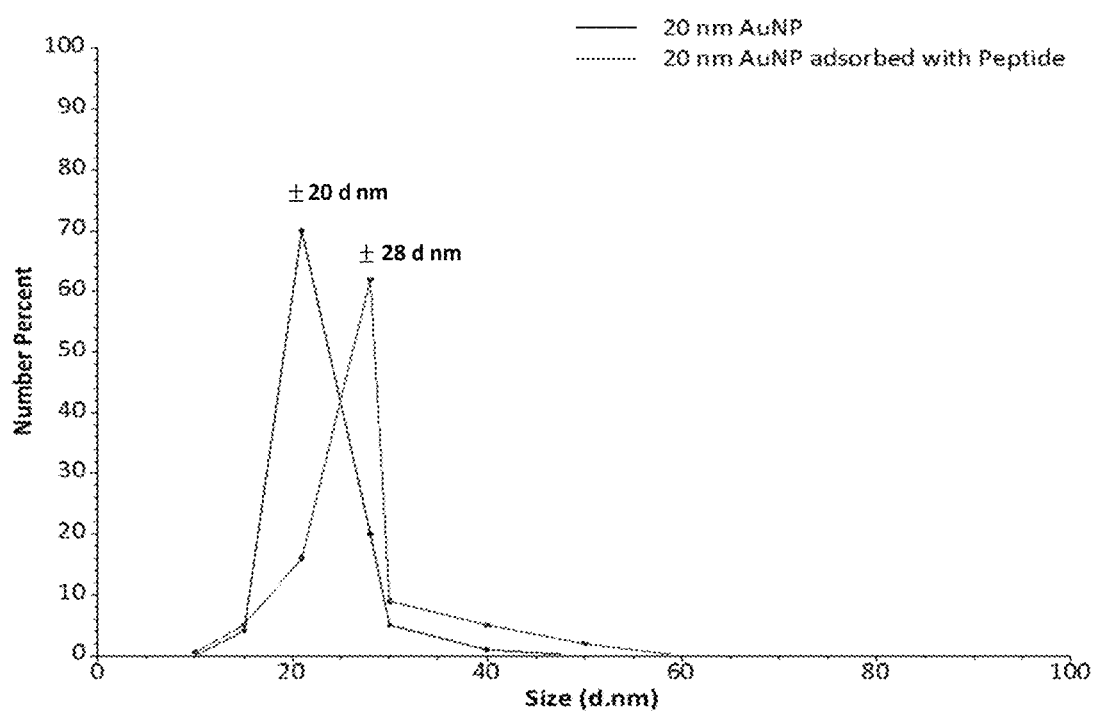
FIG. 29 shows an increase in size from 20 nm diameter (AuNP) to 28 nm diameter (AuNP adsorbed with peptide) of the nanoparticles after adsorption with peptide QLQPFPQPQLPYPQPQC (SEQ ID NO:3). The peptide was adsorbed on the surface of the gold nanoparticles in a 2-step protocol. In the first step, Avidin was adsorbed on the surface of the gold nanoparticles to obtain Avidin-AuNP particles followed by the binding of the peptide through a biotin-PEG-Maleimide linker molecule.

DLS is a well-known analytical technique used for particle size analysis in the nanometre range scale (Khlebtsov and Khlebtsov, *Colloid Journal*, 73:18-127, 2011). Following protein adsorption on the AuNP surface, the state of particle aggregation or dispersion for the colloidal gold can be accurately determined using DLS (Jans et al. *Analytical Chemistry*, 81: 9425-9432, 2009). In the Inventors' study, following the adsorption of peptide onto the surface of the AuNP, an increase in particle size was observed. DLS showed that the size of the gold colloids increased from 20 nm to 28 nm after adsorption with peptide. No additional peaks were detected, indicating the absence of self-assembly of the AuNPs into extended particle interactions following peptide adsorption on the surface (FIG. 29).

Interaction of Antibody with AuNPs Adsorbed with Peptide

Figure 30:
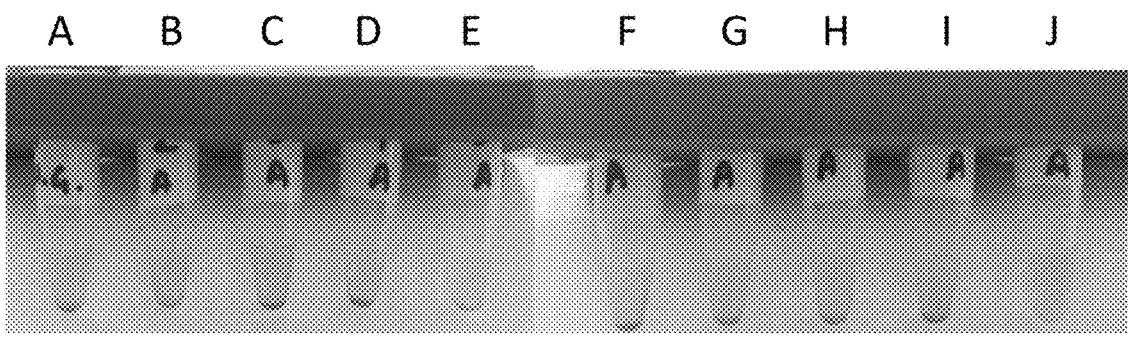
FIG. 30 shows the change in colour from red to transparent as observed in 20 nm AuNP adsorbed with peptide QLQPFPQPQLPYPQPQC (SEQ ID NO:3) in the presence of anti-gliadin at different dilutions. Change in colour from red to transparent and precipitate formation was observed in 20 nm AuNP adsorbed with peptide QLQPFPQPQLPYPQPQC in the presence of anti-gliadin antibody at dilutions (A) 2 µg/mL, (B) 4 µg/mL, (C) 6 µg/mL, (D) 8 µg/mL, (E) 10 µg/mL, (F) 12 µg/mL, (G) 14 µg/mL, (H) 16 µg/mL, (I) 18 µg/mL, and (J) 20 µg/mL and 20 nm AuNP adsorbed with peptide QLQPFPQPQLPYPQPQC alone.
Figure 31:
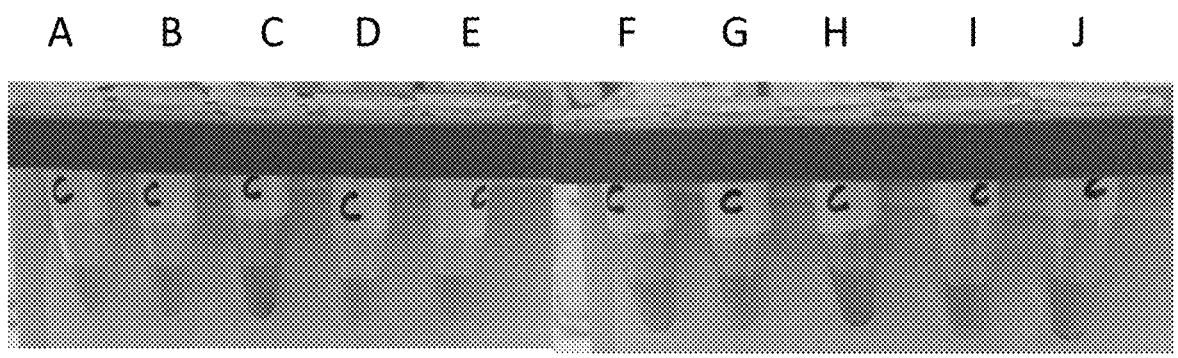
FIG. 31 shows no change in colour was observed in 20 mM AuNP adsorbed with peptide QLQPFPQPQLPYPQPQC (SEQ ID NO:3) in the presence of control antibody (IgG from rabbit serum) at different dilutions. No change in colour from red was observed in 20 nm AuNP adsorbed with peptide QLQPFPQPQLPYPQPQC in the presence of control antibody (IgG from rabbit serum) at dilutions (A) 2 µg/mL, (B) 4 µg/mL, (C) 6 µg/mL, (D) 8 µg/mL, (E) 10 µg/mL, (F) 12 µg/mL, (G) 14 µg/mL, (H) 16 µg/mL, (I) 18 µg/mL, and (J) 20 µg/mL as compared to AuNP adsorbed with peptide QLQPFPQPQLPYPQPQC alone.

Anti-gliadin antibody was added to the AuNP coated with peptide to check for aggregation and/or colour change. Spectroscopically, significant changes were observed 45 minutes after adding Anti-gliadin antibody at different concentrations to the peptide coated AuNPs. While AuNP adsorbed with peptide showed maximum absorbance at 525 nm, a decrease in absorbance as well as a shift in absorbance at 580 nm was observed for the AuNP-peptide samples incubated with Anti-gliadin antibody. A change in colour from red to transparent was clearly observed (FIG. 30).

Control normal rabbit IgG was also incubated with the peptide coated AuNPs. The results showed a small decrease in colour after adding the negative control rabbit IgG, but there was no significant shift in peak wavelength (FIG. 4). The reduction in colour and absorbance value peaks are entirely due to the dilution factor which when taken into account show no effect of the antibody on the aggregation of the peptide coated AuNPs.

Figure 32:
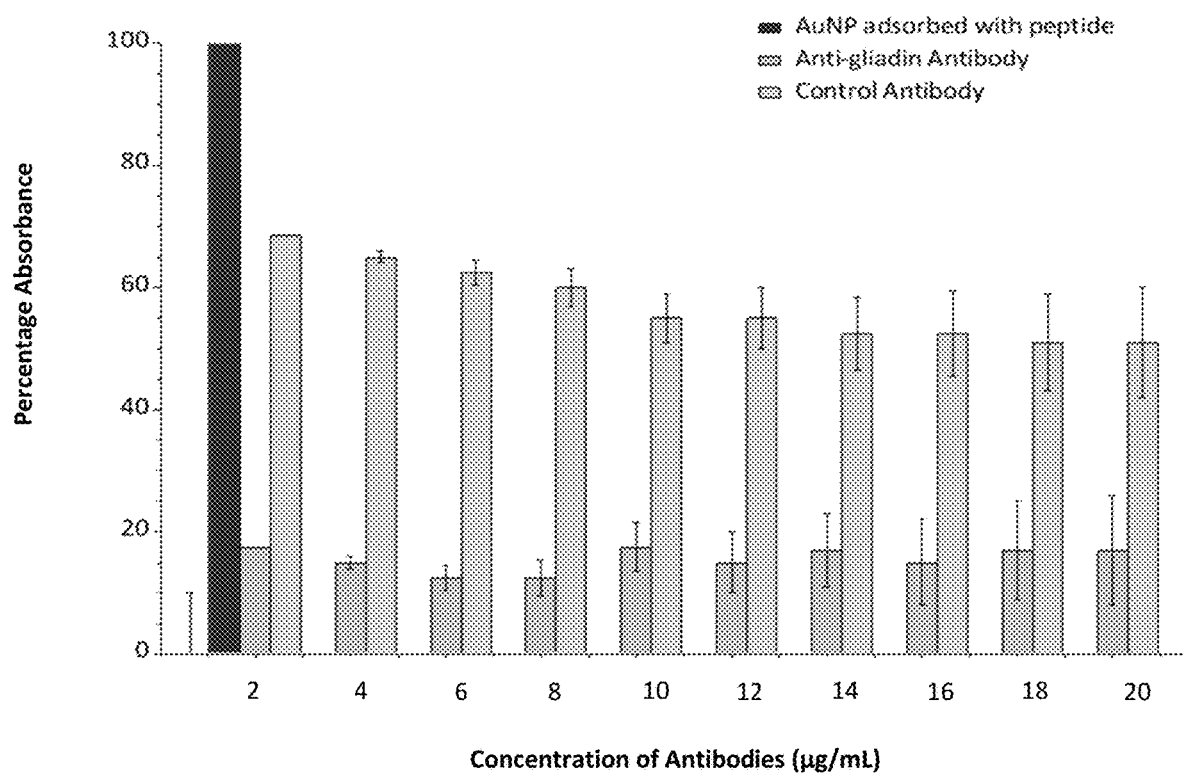
FIG. 32 shows the representation of specificity based on UV-Vis absorbance spectra for the antibody interactions at equal concentrations of anti-gliadin antibody and control antibody where (A) 2 µg/mL, (B) 4 µg/mL, (C) 6 µg/mL, (D) 8 µg/mL and (E) 10 µg/mL), (F) 12 µg/mL, (G) 14 µg/mL, (H) 16 µg/mL, (I) 18 µg/mL, and (J) 20 µg/mL as compared to AuNP adsorbed with peptide QLQPFPQPQLPYPQPQC (SEQ ID NO:3) alone. Control bars are shown on the right.

The results using peptide specific and normal rabbit IgG are summarized in the graph shown in FIG. 32. As can be seen, at all concentrations the absorbance was significantly lower using anti-gliadin IgG as compared to normal IgG particularly in the range of 4-8 μg/mL. Even at 2 μg/mL the difference between control and peptide specific IgG was highly significant. This range of antibody is what is expected in human serum and saliva.

Figure 33:
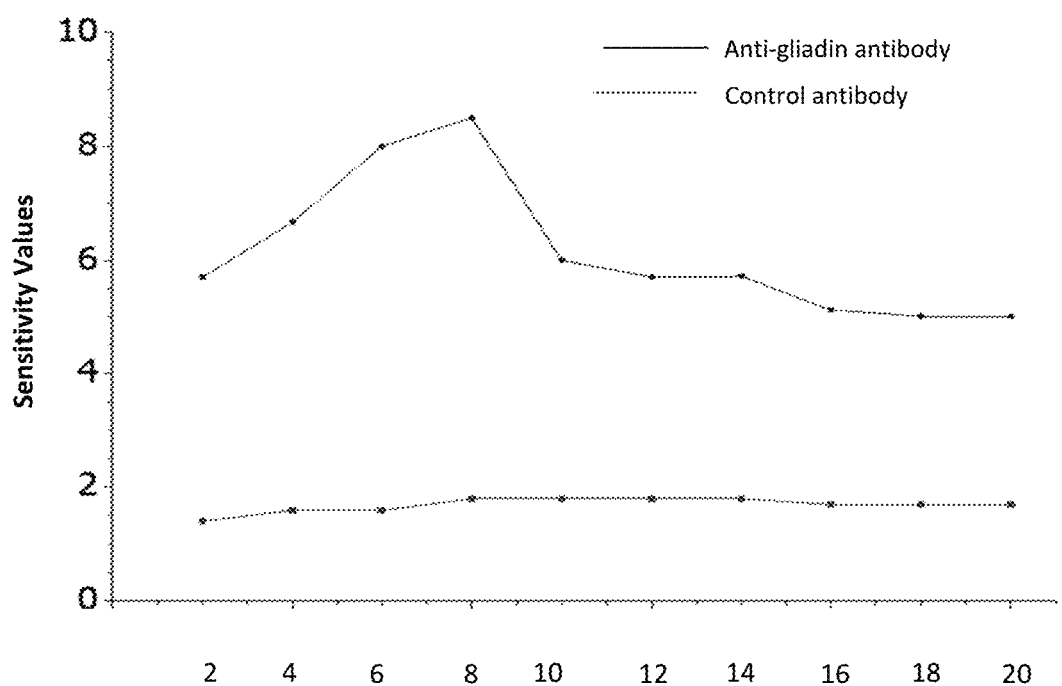
FIG. 33 shows the colorimetric response curve plotted on AuNP adsorbed with peptide QLQPFPQPQLPYPQPQC (SEQ ID NO:3) in the presence of anti-gliadin antibody (top line) and the control antibody (IgG from rabbit serum; bottom line) at dilutions 2 µg/mL, 4 µg/mL, 6 µg/mL, 8 µg/mL, 10 µg/mL, 12 µg/mL, 14 µg/mL, 16 µg/mL, 18 µg/mL and 20 µg/mL.

As can be seen in FIG. 33, an increase in the colorimetric response was observed, reaching a maximum value when anti-gliadin antibody is added at a concentration of 8 μg/mL to the AuNP adsorbed with peptide. The curve begins to drop when the anti-gliadin antibody concentration reaches 10 μg/mL. For the control antibody, the response curve is constant with only a slight increase at the control antibody dilution of 10 μg/mL. The near constant colorimetric response curve obtained for the control antibody as compared to the response curve obtained for anti-gliadin antibody demonstrates the specificity of the assay.

Transmission Electron Microscopy (TEM)

Figure 34:
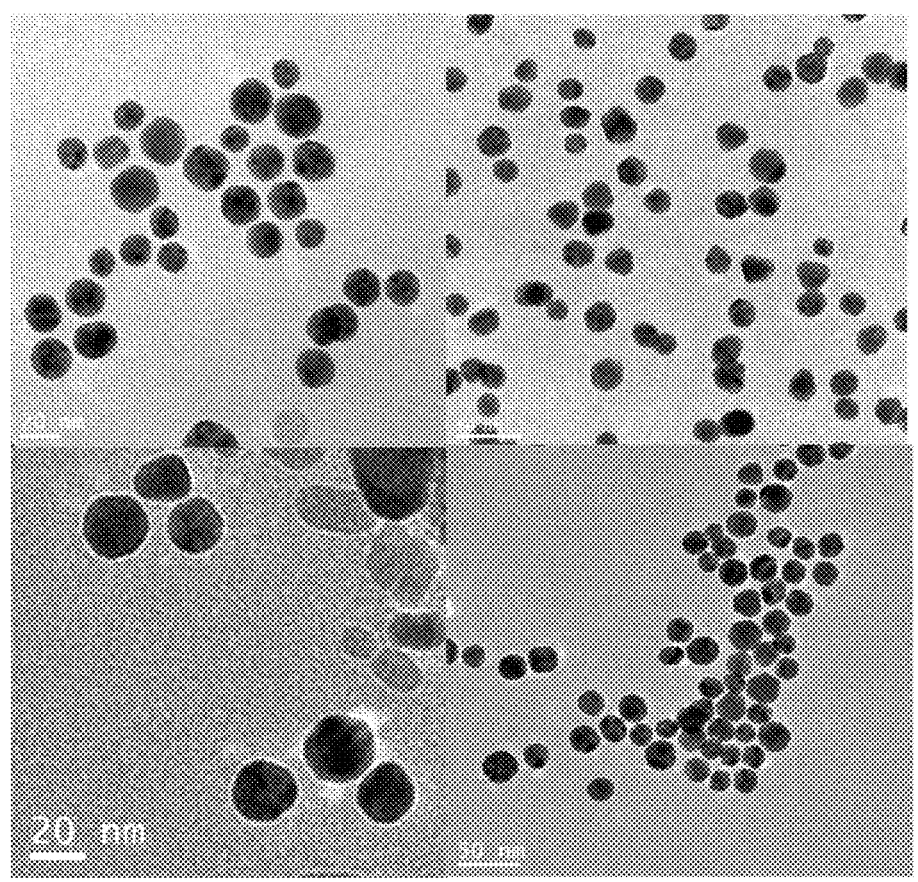
FIG. 34 shows high resolution Transmission Electron Microscopy (TEM) micrographs showing the adsorption of peptide QLQPFPQPQLPYPQPQC (SEQ ID NO:3) on the surface of 20 nm AuNP of (A & B) gold nanoparticle, (C & D) gold nanoparticle adsorbed with peptide showing a white layer 'halo' surrounding the surface of the nanoparticles indicating coating of the gold with peptide QLQPFPQPQLPYPQPQC. The 'halo effect' is not present on the un-adsorbed gold nanoparticles. The halo indicates that multiple gliadin molecules are adsorbed on each nanoparticle.

TEM analysis of uncoated 20 nm gold nanoparticles shows a uniform spherical shape. In contrast, high resolution imaging of 20 nm gold nanoparticles adsorbed with peptide via the 2-step protocol described above, revealed a thin white layer of material (<1 nm) surrounding the nanoparticles, which is not present on 20 nm AuNP (FIG. 34).

Figure 35:
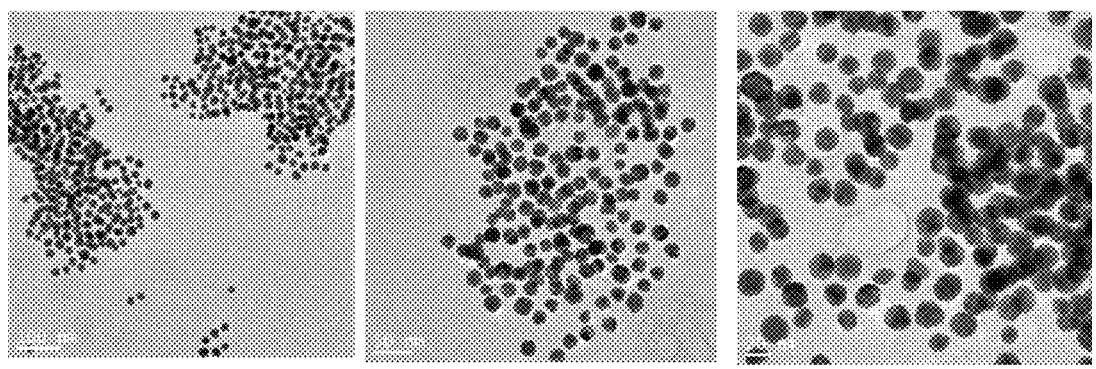
FIG. 35 shows high resolution Transmission Electron Microscopy (TEM) micrographs of gold nanoparticle adsorbed with peptide QLQPFPQPQLPYPQPQC (SEQ ID NO:3) showing aggregation of nanoparticles following the interaction of AuNP-Peptide with anti-gliadin antibody.
Figure 36:
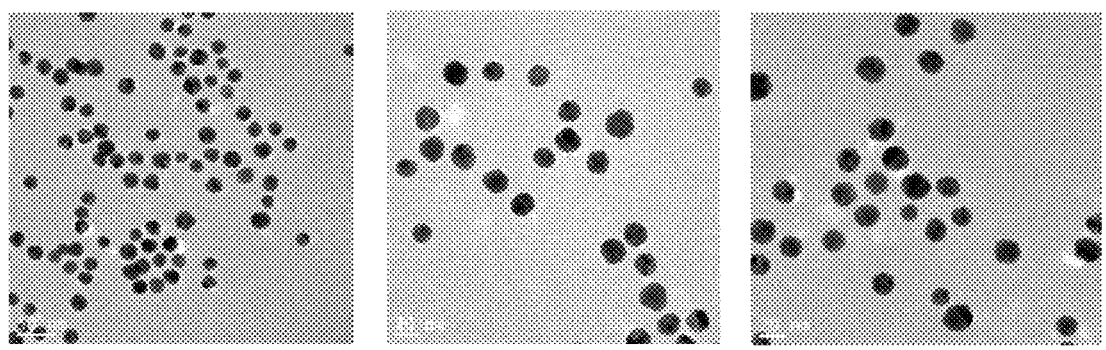
FIG. 36 shows high resolution Transmission Electron Microscopy (TEM) micrographs of nanoparticles showing no aggregation following the interaction of AuNP-peptide with control antibody.

As the layer was very thin, further TEM analysis of the samples following addition of the antibodies was done to demonstrate the adsorption of the AuNPs with the peptide sequence. It was observed that following the addition of Anti-gliadin antibody at a concentration of 12 μg/mL, the AuNP particles adsorbed with peptide showed formation of aggregation. On the other hand, the addition of the control antibody (IgG) at the same concentration, did not cause any aggregation and the AuNPs remained dispersed (FIG. 35 and FIG. 36).

Parameters for Assay Validation for Testing Clinical Samples

Serum samples obtained from patients affected from coeliac disease were tested using the assay developed based on the AuNPs adsorbed with peptide. As outlined in the methods, serum was diluted at 1:20, concentrated and purified and then allowed to react with AuNPs adsorbed with peptide.

The assay sensitivity was determined based on the colorimetric response obtained for each serum sample and is calculated as Colorimetric Response=I max at 580 nm/I at 532 nm. Using this method, the calculated colorimetric response for normal serum i.e. serum without Anti-gliadin antibody is 1 and this acts as the cut-off value. Therefore, for the clinical samples, based on the spectral absorbance data, a value of 1 or less than 1 is indicated as negative for coeliac disease and a value above 1 is indicated as coeliac disease positive. The results of the analysis using AuNP-peptide interaction in serum are described in Table 5 below along with the results reported using the existing serology and histology tests, including those based on the detection of anti-transglutaminase antibodies (tTG-IgA) and anti-deamidated gliadin protein antibodies (DGP-IgG; DGP-IgA).

TABLE 5

Comparison of patient samples using the AuNP-peptide test with existing histology and serological* testing methods

| Volunteer | Histology | tTG-IgA | DGP-IgG | DGP-IgA | New AuNP-Gliadin based Test | New AuNP-Peptide based Test |
|---|---|---|---|---|---|---|
| n.1 | CD inconclusive | 5 (<20) | 17 (<20) | | CD | CD |
| n.2 | CD | 1 (<4) | 3 (<20) | | CD | CD |
| n.3 | Non-CD | 0.1 (0-6) | 0.2 (0-6) | | Non-CD | CD |
| n.4 | CD | >100 (<4) | 33 (<20) | | CD | CD |
| n.5 | CD/T1DM | 121 (<20) | | | CD | CD |
| n.6 | CD | >100 (<4) | >100 (<20) | | CD | CD |
| n.7 | CD | 217 (<5) | >150 (<20) | 132 (<20) | CD | CD |
| n.8 | CD | 13 (0-6) | 23 (0-6) | | CD | Non-CD |
| n.9 | CD | >100 (<5) | >100 (<20) | | CD | CD |
| n.10 | CD | 11 (0-6) | 1.4 (0-6) | | CD | CD |
| n.11 | CD | 9 (<4) | 97 (<20) | | CD | CD |
| n.12 | CD | 18.2 (0 < 20) | 3 (0.20) | | Non-CD | CD |
| n.13 | CD | 16 (0-20) | 7 (<20) | 5 (<20) | CD | CD |
| n.14 | Non-CD | 4 (0-20) | | | Non-CD | Non-CD |
| n.15 | CD | 47 (<5) | 86 (<5) | | CD | CD |
| n.16 | CD | 74 (0-20) | | | CD | Non-CD |
| n.17 | CD | 145 (0-20) | | | CD | CD |
| n.18 | Non-CD | <5 (<5) | 22 (<20) | | CD | CD |
| n.19 | Non-CD | 12 (0-6) | 18 (0-6) | | CD | CD |
| n.20 | Non-CD | 11 (0-6) | 13 (0-6) | | CD | CD |
| n.21 | CD | 57 (<4) | 93 (<20) | | CD | CD |
| n.22 | CD | 149 (<20) | 63 (<20) | 31 (<20) | CD | CD |
| n.23 | Non-CD | <5 (<5) | <20 (<20) | | CD | CD |
| n.24 | CD | >100 (<4) | >100 (<20) | | CD | CD |

TABLE 5-continued

Comparison of patient samples using the AuNP-peptide test
with existing histology and serological* testing methods

| Volunteer | Histology | tTG-IgA | DGP-IgG | DGP-IgA | New AuNP-Gliadin based Test | New AuNP-Peptide based Test |
|---|---|---|---|---|---|---|
| n.25 | Non-CD | 3.8 (<6) | 37 (<6) | | CD | CD |
| n.26 | Indeterminate | 28 (0-6) | 22 (0-6) | | CD | CD |
| n.27 | Non-CD | <5 (<5) | <20 (<20) | | Non-CD | Non-CD |
| n.28 | CD | 180 (0-6) | 21 (0-6) | | CD | CD |
| n.29 | Indeterminate | 4.8 (0-6) | 22 (0-6) | | CD | CD |
| n.30 | CD | 20 (0-6) | 8.1 (0-6) | | CD | CD |

*Serology results are indicated as IgA or IgG levels followed by reference ranges in brackets.

Analysis of Clinical Samples Using AuNP-Peptide Based Test

Figure 37:
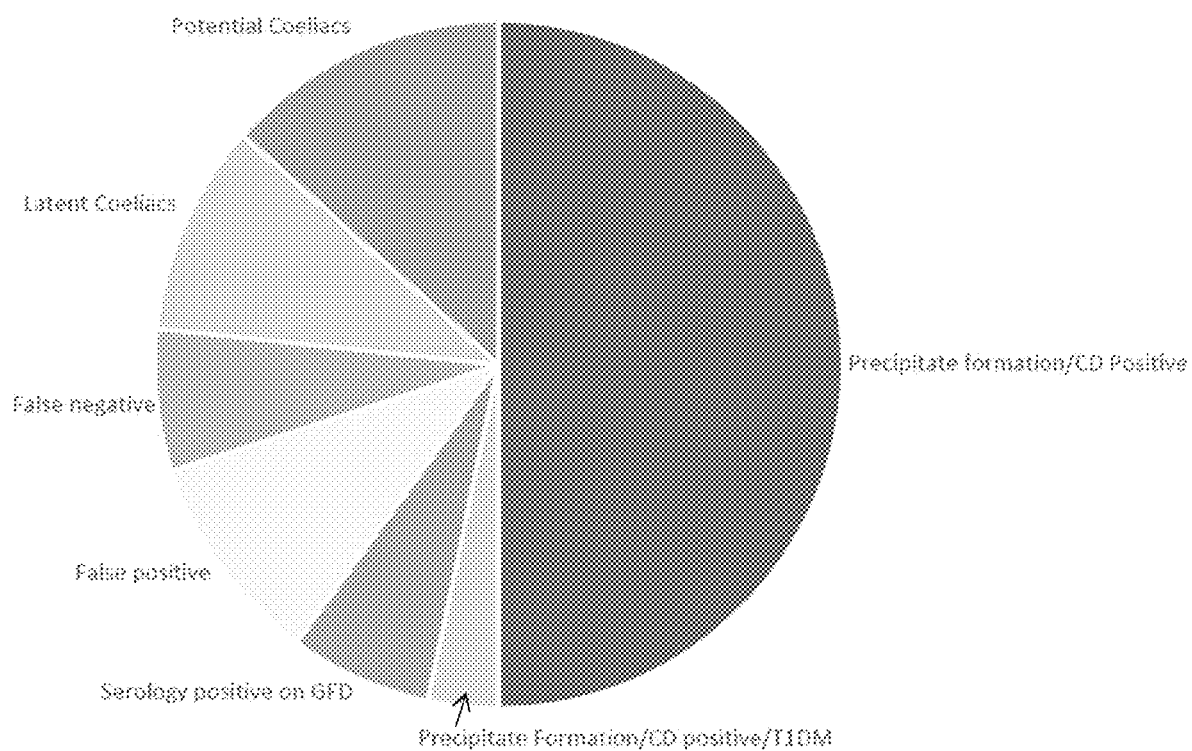
FIG. 37 shows the representation of the distribution of clinical samples using AuNP-peptide test.

The results of the randomized and blinded clinical samples tested in the inventors' assay were compared with the results reported using the existing serological and histology methods. These results for the 30 clinical samples are reported after the visual examination of precipitate formation and determination of shift or change in absorbance values using UV-Vis spectrophotometer. The distribution of these samples is described FIG. 37.

Out of these thirty samples, fifteen samples that were diagnosed with active coeliac disease with high antibody titres as shown by serology and intestinal damage as per biopsy were identified as coeliac disease positive using the inventors' AuNP-peptide as well. These samples showed the formation of a precipitate and had a clear shift as well as drop in UV-Vis absorbance values as well as a high colorimetric response value.

The three samples with inconclusive/indeterminate biopsy reports could also be identified as positive for coeliac disease using the peptide based diagnostic test, as a clear precipitate similar as the one following the addition of the serum to the AuNP nanoparticles adsorbed with gliadin, was observed. The UV-Vis absorbance data supported the visual examination and these three samples were referred as positive for coeliac disease.

The four clinical cases identified as potential coeliac disease sufferers by the inventors' diagnostic test method using gliadin adsorbed nanoparticles were again identified as coeliac potentials using peptide functionalised nanoparticles. In addition, the diagnostic test based on peptide functionalised nanoparticles, could correctly identify the young patient with T1DM as positive for coeliac disease and this matches with the previously conducted biopsy and serology profile of the patient. This again demonstrates the higher sensitivity of the nanoparticle based test even in the presence of low titres of anti-gliadin antibody in the sera.

The peptide functionalised nanoparticle based diagnostic test for nanoparticles, however, suffers from lowered sensitivity particularly when diagnosing patients placed on a gluten free diet (GFD). The gliadin based nanoparticle test, was more discriminatory and sensitive to the anti-gliadin antibody titres in serum. That test could clearly distinguish the person following a GFD for more than 2 months to the person who had been on a GFD for less than 2 weeks. The peptide functionalised nanoparticle test, however, is less sensitive as it gives a positive for coeliac disease in the person following the gluten free diet for more than 2 months.

Overall, upon comparing the results for the 30 clinical samples, while 25 samples showed comparable results, 3 false positive results and 2 false negative results were obtained using the nanoparticle based diagnostic test method using peptide sequence giving the inventors' test an overall sensitivity and specificity of 83.3%.

The invention claimed is:

1. A method of detecting an anti-gliadin antibody in a sample, the method comprising
   (i) contacting the sample of a body fluid obtained from an individual with a nanoparticle adsorbed with a gliadin molecule, and
   (ii) detecting an optical property of the nanoparticle adsorbed with a gliadin molecule, wherein a change in the optical property of the nanoparticle adsorbed with a gliadin molecule is indicative of the presence of an anti-gliadin antibody in the sample,
wherein the optical property of the nanoparticle adsorbed with a gliadin molecule is absorbance and the change is absorption at a longer wavelength, which is detected in the visible absorption spectrum, and wherein an anti-gliadin antibody, if present in the sample, binds to one or more nanoparticles adsorbed with a gliadin molecule, resulting in aggregation of the nanoparticles adsorbed with a gliadin molecule.

2. The method according to claim 1, wherein the anti-gliadin antibody is an IgG anti-gliadin antibody or an IgA anti-gliadin antibody.

3. The method according to claim 1, wherein the presence of an anti-gliadin antibody in the sample is indicative that the individual has a gluten-related disorder.

4. The method according to claim 3, wherein the gluten-related disorder is coeliac disease.

5. The method according to claim 1, wherein the body fluid is saliva, serum, blood, urine or a gastrointestinal secretion.

6. The method according to claim 1, wherein the change in the optical property of the nanoparticle adsorbed with a gliadin molecule is detected within less than about ten minutes, or less than about five minutes, or less than about four minutes, or less than about three minutes or less than about two minutes, or less than about one minute of performing step (i).

7. The method according to claim 1, wherein: the nanoparticle is a gold nanoparticle.

8. The method according to claim 1, wherein the nanoparticle has a diameter of about 1 nm to about 300 nm.

9. The method according to claim 1, wherein the nanoparticle has a diameter of about 5 nm to about 20 nm.

10. The method according to claim 1, wherein the nanoparticle has a diameter of about 20 nm.

11. The method according to claim 1, wherein the gliadin molecule is gliadin extract from wheat.

* * * * *